US008138336B2

(12) United States Patent
Magnuson et al.

(10) Patent No.: US 8,138,336 B2
(45) Date of Patent: *Mar. 20, 2012

(54) PYRROLOTRIAZINE DERIVATIVES USEFUL FOR TREATING CANCER THROUGH INHIBITION OF AURORA KINASE

(75) Inventors: Steven Magnuson, Wallingford, CT (US); Philip Wickens, Richmond Hill (CA); Zhonghua Zhang, Ridgefield, CT (US); Ning Qi, Rahway, NJ (US); Xin Ma, Beijing (CN)

(73) Assignee: Bayer HealthCare LLC, Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/679,787

(22) PCT Filed: Sep. 22, 2008

(86) PCT No.: PCT/US2008/077211
§ 371 (c)(1),
(2), (4) Date: Jun. 28, 2010

(87) PCT Pub. No.: WO2009/042543
PCT Pub. Date: Apr. 2, 2009

(65) Prior Publication Data
US 2010/0273800 A1 Oct. 28, 2010

Related U.S. Application Data

(60) Provisional application No. 60/995,147, filed on Sep. 25, 2007.

(51) Int. Cl.
*C07D 487/04* (2006.01)
*C07D 417/02* (2006.01)
*C07D 413/02* (2006.01)
*A61K 31/53* (2006.01)
*A61P 35/00* (2006.01)

(52) U.S. Cl. ...................................... 544/183; 514/243
(58) Field of Classification Search .................. 544/183; 514/243
See application file for complete search history.

(56) References Cited

U.S. PATENT DOCUMENTS

| 7,563,791 B2 * | 7/2009 | Dixon et al. ................. 514/243 |
| 2005/0153966 A1 | 7/2005 | Gangloff et al. |
| 2007/0004733 A1 | 1/2007 | Chen et al. |
| 2007/0208013 A1 * | 9/2007 | Dixon et al. ................. 514/227.8 |
| 2009/0281079 A1 * | 11/2009 | Dixon et al. ............. 514/211.15 |
| 2010/0063038 A1 * | 3/2010 | Dixon et al. ................. 514/228.5 |
| 2010/0075958 A1 | 3/2010 | Dixon et al. |
| 2010/0179125 A1 | 7/2010 | Dixon et al. |

FOREIGN PATENT DOCUMENTS

| WO | WO-00/71129 A1 | 11/2000 |
| WO | WO-2005/121147 A1 | 12/2005 |
| WO | WO-2007/061882 A2 | 5/2007 |

OTHER PUBLICATIONS

Cecil Textbook of Medicine, edited by Bennet, J.C., and Plum F., 20th edition,vol. 1, 1004-1010, 1996.*
West, Anthony R., Solid State Chemistry and its Applications, Wiley, New York, 1988, pp. 358 & 365.*
Vippagunta et al., Advanced Drug Delivery Reviews 48: 3-26, 2001.*
Gautschi et al., Clin. Cancer Res., 14(6), 1639-1648, 2008.*
Mountzios et al., Cancer Treatments Reviews, 34, 175-182, 2008.*
Mass, R. D., Int. J. Radiation Oncology Bio. Phys. vol. 58(3): 932-940, 2004.*
Fabbro et al. Pharmacology & therapeutics 93, 79-98, 2002.*
Freshney et al.,Culture of Animal Cells, A Manual of Basic Technique, Alan R. Liss, Inc., 1983, New York, p. 4.*
Dermer et al., Bio/Technology, 1994, 12:320.*
Powell et al., British Journal of Dermatology, 141 802-810, 1999.*
Cohen et al., Current Opinion in Chemical Biology, 3,459-465, 1999.*
Golub et al., Science, 286, 531-537, 1999.*
Simone, Oncology: Introduction, Cecil Textbook of Medicine, edited by Bennet, J.C., and Plum F., 20th edition, vol. 1, 1004-1010, 1996.
Freshney et al. "Culture of Animal Cells, A Manual of Basic Technique," Alan R. Liss, Inc. 1983, New York, p. 4.
Powell et al., British Journal of Dermatology, 141: 802-810, 1999.
Cohen et al., Current Opinion in Chemical Biology, 3, 456-465, 1999.
Mass, R.D., International Journal of Radiation Oncology Bio Phys. vol. 58(3): 932-940, 2004.
Fabbro et al., Pharmacology & Therapeutics 93, 79-98, 2002.
West—Solid State Chemistry 1987.
Vippagunta et al., Advanced Drug Delivery Reviews 48; 3-26, 2001.
Gautschi et al., Clin. Cancer Research, 19(6), 1639-1648, 2008.
Mountzios et al., Cancer Treatments Reviews, 34, 175-182, 2006.
Ferrara, N., Oncology, 69 suppl. 3, 11-16, 2005.
Jain et al., Nature Clinical Practice Oncology, 3(1), 24-40, 2006.
Ferrara, N. The Oncologist: 9 (Suppl. 1): 2-10, 2004.

* cited by examiner

*Primary Examiner* — Venkataraman Balasubramanian
(74) *Attorney, Agent, or Firm* — Edwards Wildman Palmer LLP; Barry Kramer; Nicholas J. DiCeglie, Jr.

(57) ABSTRACT

This invention relates to novel compounds and processes for their preparation, methods of treating diseases, particularly Cancer, comprising administering said compounds, and methods of making pharmaceutical compositions for the treatment or prevention of disorders, particularly Cancer.

15 Claims, No Drawings

PYRROLOTRIAZINE DERIVATIVES USEFUL FOR TREATING CANCER THROUGH INHIBITION OF AURORA KINASE

CROSS-REFERENCE TO RELATED APPLICATION

This application is the National Stage of PCT/US2008/077211, filed Sep. 22, 2008, and Amended Under PCT Article 19 on Feb. 2, 2009, and PCT Article 34 on Jul. 24, 2009, which claims the benefit of the U.S. Provisional Application No. 60/995,147, filed Sep. 25, 2007, the entire contents of each of which are incorporated herein by reference.

FIELD OF THE INVENTION

This invention relates to novel compounds and processes for their preparation, methods of treating diseases, particularly Cancer, comprising administering said compounds, and methods of making pharmaceutical compositions for the treatment or prevention of disorders, particularly Cancer.

BACKGROUND OF THE INVENTION

Dysregulated cellular proliferation, genomic instability and survival are hallmarks of all cancers. Normal cellular regulation is a balance of signals that control cell proliferation and programmed cell death (apoptosis). The interplay between these complex processes maintains tissue stability and function. A loss of regulation of these cellular pathways that control cell cycle progression leads to uncontrolled cell growth and tissue homeostasis.

Cell cycle regulation is controlled through an ordered cascade of protein phosphorylation events. Several families of protein kinases that play critical roles in cell cycle progression have been identified. Interestingly, the activity of many of these kinases is increased in human tumors when compared to normal tissue. Whether this is due to increased levels of expression or protein or by changes in expression of co-activators, the ultimate result is a loss of cell cycle regulation.

The Aurora family (Aurora-A, B, C or 2, 1, 3) are serine/threonine kinases that are essential to the regulation and function of mitosis and cytokinesis (summarized in Adams et al., 2001, Trends in Cell Biology 11 (2): 49-54). The expression and activity of Aurora Kinase is cell cycle regulated such that peak activity occurs during mitosis and expression is nearly undetectable in a resting cell. The catalytic domains of the Auroras are highly conserved, with greater than 90% homology, but have distinct subcellular localizations and functions during mitosis and cytokinesis. Aurora Kinase A is localized to centrosomes and spindle poles in mitosis and is required for centrosome segregation and maturation. In contrast, Aurora-B forms a complex with three other proteins, inner centromere protein (INCENP), borealin and survivin, and behaves as a "mitotic passenger protein" (Meraldip P, et al 2004). This chromosomal passenger protein plays a central role in complex functions to chaperone and regulate mitosis and cytokinesis. The movement of the complex from centromeres to the central spindle during anaphase, to the midbody presumably reflects the requirement of Aurora-B to act on different substrates. A range of substrates has been identified for Aurora Kinase A and B with histone 3, a protein involved in chromatin condensation and mitotic entry, being the best characterized. Finally, Aurora C has been shown to be localized to spindle poles during the late stages of mitosis, however very little is known about its overall function (Kimuram M, et al 1999).

Small molecule inhibitors of Aurora Kinases have provided insight into the overall understanding of the role of Auroras in mitotic regulation (Ditchfield C, et al 2003, Hanning E A, et al 2004, and Carpinelli P, et al 2005). Structurally diverse inhibitors promote the same cellular phenotypes and inhibition of histone 3 phosphorylation on serine 10. Additionally, small molecule inhibitors of Aurora Kinase and antisense oligonucleotides have been demonstrated to have an antiproliferative effect on tumor cells. This indicates that inhibition of Aurora Kinase will be useful in the treatment of cancer.

SUMMARY OF THE INVENTION

In one embodiment, the present invention provides a compound of formula (I)

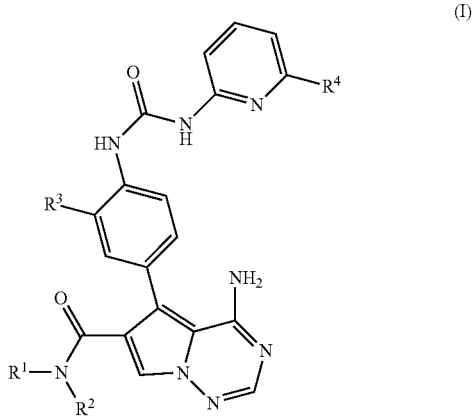

(I)

or a physiologically acceptable salt, solvate, hydrate or stereoisomer thereof, wherein:

$R^1$ is —$(C_1-C_4)$alkyl, —$(C_1-C_4)$alkyl-$CF_3$, —$(C_3-C_6)$cycloalkyl, or —$(C_2-C_4)$alkyl -$NR^5R^6$;

$R^2$ is hydrogen or —$(C_1-C_4)$alkyl;

$R^3$ is halogen;

$R^4$ is —$(C_1-C_4)$alkyl, optionally substituted with one or more hydroxy, amino, alkoxy, or cycloalkyl groups; and $R^5$ and $R^6$, may be the same or different, and are independently hydrogen, methyl, ethyl, or $R^5$ and $R^6$ may be taken together with the nitrogen to which they are bound to form a pyrrolidine ring.

In a preferred embodiment, the invention provides a compound of formula (I), wherein $R^1$ is methyl, ethyl, n-propyl, sec-butyl, iso-butyl, tert-butyl, cyclopropyl, 2,2,2-trifluoroethyl, or 2-(dimethylamino)-ethyl.

In another preferred embodiment, the invention provides a compound of formula (I), wherein $R^2$ is hydrogen.

In still another preferred embodiment, the invention provides a compound of formula (I), wherein $R^3$ is fluorine or chlorine.

In yet another preferred embodiment, the invention provides a compound of formula (I),wherein $R^4$ is methyl or ethyl.

In still yet another preferred embodiment, the invention provides a compound of formula (I). The compound of claim 1, wherein $R^3$ is fluorine or chlorine and $R^4$ is methyl or ethyl.

In a distinct embodiment, the invention provides a compound of formula (I), which is a salt of formula (I), more preferably an an acetate, an adipate, an alginate, an ascorbate, an aspartate, a benzoate, a benzenesulfonate, a bis(benzenesulfonate), a bisulfate, a butyrate, a bis(maleate), a fumarate, a hemi-fumarate, a citrate, a camphorate, a camphorsulfonate, a cinnamate, a cyclopentanepropionate, a digluconate, a dodecylsulfate, a ethanesulfonate, a fumarate, a glucoheptanoate, a glycerophosphate, a hemisulfate, a heptanoate, a hexanoate, a hydrochloride, a hydrobromide, a hydroiodide, a 2-hydroxyethanesulfonate, an itaconate, a lactate, a maleate, a mandelate, a methanesulfonate, a 2-naphthalenesulfonate, a nicotinate, a nitrate, an oxalate, a pamoate, a pectinate, a persulfate, a 3-phenylpropionate, a picrate, a pivalate, a propionate, a succinate, a sulfonate, a bis(methanesulfonate), a tartrate, a thiocyanate, a tosylate, or an undecanoate salt; most preferably a bis(methanesulfonate), a hydrochloride, a bis(maleate), a hemi-fumarate, a hydrobromide, an oxalate, or a bis(benzenesulfonate) salt.

In a distinct embodiment, the invention provides a compound having the IUPAC name:

- 4-amino-5-(3-fluoro-4-{[(6-methylpyridin-2-yl)carbamoyl]amino}phenyl)-N-methylpyrrolo[2,1-f][1,2,4]triazine-6-carboxamide;
- 4-amino-N-ethyl-5-(3-fluoro-4-{[(6-methylpyridin-2-yl)carbamoyl]amino}phenyl)pyrrolo[2,1-f][1,2,4]triazine-6-carboxamide;
- 4-amino-5-(3-fluoro-4-{[(6-methylpyridin-2-yl)carbamoyl]amino}phenyl)-N-propylpyrrolo[2,1-f][1,2,4]triazine-6-carboxamide;
- 4-amino-5-(3-fluoro-4-{[(6-methylpyridin-2-yl)carbamoyl]amino}phenyl)-N-(2,2,2-trifluoroethyl)pyrrolo[2,1-f][1,2,4]triazine-6-carboxamide;
- 4-amino-5-(3-fluoro-4-{[(6-methylpyridin-2-yl)carbamoyl]amino}phenyl)-N-isobutylpyrrolo[2,1-f][1,2,4]triazine-6-carboxamide;
- 4-amino-N-cyclopropyl-5-(3-fluoro-4-{[(6-methylpyridin-2-yl)carbamoyl]amino}phenyl)pyrrolo[2,1-f][1,2,4]triazine-6-carboxamide;
- 4-amino-N-ethyl-5-(3-fluoro-4-{[(6-methylpyridin-2-yl)carbamoyl]amino}phenyl)-N-methylpyrrolo[2,1-f][1,2,4]triazine-6-carboxamide;
- 4-amino-N-[2-(dimethylamino)ethyl]-5-(3-fluoro-4-{[(6-methylpyridin-2-yl)carbamoyl]amino}phenyl)pyrrolo[2,1-f][1,2,4]triazine-6-carboxamide;
- 4-amino-N-tert-butyl-5-(3-fluoro-4-{[(6-methylpyridin-2-yl)carbamoyl]amino}phenyl)pyrrolo[2,1-f][1,2,4]triazine-6-carboxamide;
- 4-amino-N-tert-butyl-5-(4-{[(6-ethylpyridin-2-yl)carbamoyl]amino}-3-fluorophenyl)pyrrolo[2,1-f][1,2,4]triazine-6-carboxamide;
- 4-amino-5-(4-{[(6-ethylpyridin-2-yl)carbamoyl]amino}-3-fluorophenyl)-N-(2,2,2-trifluoroethyl)pyrrolo[2,1-f][1,2,4]triazine-6-carboxamide;
- 4-amino-5-(3-chloro-4-{[(6-methylpyridin-2-yl)carbamoyl]amino}phenyl)-N-ethylpyrrolo[2,1-f][1,2,4]triazine-6-carboxamide;
- 4-amino-5-(3-chloro-4-{[(6-methylpyridin-2-yl)carbamoyl]amino}phenyl)-N-propylpyrrolo[2,1-f][1,2,4]triazine-6-carboxamide;
- 4-amino-5-(3-chloro-4-{[(6-methylpyridin-2-yl)carbamoyl]amino}phenyl)-N-cyclopropylpyrrolo[2,1-f][1,2,4]triazine-6-carboxamide;
- 4-amino-5-(3-chloro-4-{[(6-methylpyridin-2-yl)carbamoyl]amino}phenyl)-N-[2-(dimethylamino)ethyl]pyrrolo[2,1-f][1,2,4]triazine-6-carboxamide;
- 4-amino-5-(3-chloro-4-{[(6-methylpyridin-2-yl)carbamoyl]amino}phenyl)-N-(2,2,2-trifluoroethyl)pyrrolo[2,1-f][1,2,4]triazine-6-carboxamide;
- 4-amino-5-(3-chloro-4-{[(6-ethylpyridin-2-yl)carbamoyl]amino}phenyl)-N-(2,2,2-trifluoroethyl)pyrrolo[2,1-f][1,2,4]triazine-6-carboxamide;
- or a physiologically acceptable salt, solvate, hydrate or stereoisomer thereof In another distinct embodiment, the invention provides a salt having the IUPAC name:

- 4-amino-5-(3-fluoro-4-{[(6-methylpyridin-2-yl)carbamoyl]amino}phenyl)-N-(2,2,2-trifluoroethyl)pyrrolo[2,1-f][1,2,4]triazine-6-carboxamide dimethanesulfonate;
- 4-amino-5-(3-fluoro-4-{[(6-methylpyridin-2-yl)carbamoyl]amino}phenyl)-N-(2,2,2-trifluoroethyl)pyrrolo[2,1-f][1,2,4]triazine-6-carboxamide hydrochloride;
- 4-amino-5-(3-fluoro-4-{[(6-methylpyridin-2-yl)carbamoyl]amino}phenyl)-N-(2,2,2-trifluoroethyl)pyrrolo[2,1-f][1,2,4]triazine-6-carboxamide di[(2Z)-but-2-enedioate];
- 4-amino-5-(3-fluoro-4-{[(6-methylpyridin-2-yl)carbamoyl]amino}phenyl)-N-(2,2,2-trifluoroethyl)pyrrolo[2,1-f][1,2,4]triazine-6-carboxamide (2E)-but-2-enedioate (2:1);
- 4-amino-5-(3-fluoro-4-{[(6-methylpyridin-2-yl)carbamoyl]amino}phenyl)-N-(2,2,2-trifluoroethyl)pyrrolo[2,1-f][1,2,4]triazine-6-carboxamide hydrobromide;
- 4-amino-5-(4-{[(6-methylpyridin-2-yl)carbamoyl]amino}phenyl)-N-(2,2,2-trifluoroethyl)pyrrolo[2,1-f][1,2,4]triazine-6-carboxamide oxalate; or
- 4-amino-5-(4-{[(6-methylpyridin-2-yl)carbamoyl]amino}phenyl)-N-(2,2,2-trifluoroethyl)pyrrolo[2,1-f][1,2,4]triazine-6-carboxamide bisbenzenesulfonate.

Depending on their structure, the compounds according to the invention can exist in stereoisomeric forms (enantiomers or diastereomers). The invention therefore relates to the enantiomers or diastereomers and to their respective mixtures. Such mixtures of enantiomers or diastereomers can be separated into stereoisomerically unitary constituents in a known manner.

The invention also relates to tautomers of the depicted compounds, depending on the structure of the respective compound.

Definitions

Unless otherwise stated, the following definitions apply for the technical expressions used throughout this specification and claims:

"Salts" for the purposes of the invention are preferably pharmaceutically acceptable salts of the compounds according to the invention. For example, see S. M. Berge, et al. "Pharmaceutical Salts," *J. Pharm. Sci.* 1977, 66, 1-19.

"Pharmaceutically acceptable salts" include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, propionic acid, lactic acid, tartaric acid, malic acid, citric acid, fumaric acid, maleic acid and benzoic acid.

"Pharmaceutically acceptable salts" also include salts of customary bases, such as for example and preferably alkali metal salts (for example sodium and potassium salts, alkaline earth metal salts (for example calcium and magnesium salts) and ammonium salts derived from ammonia or organic amines having 1 to 16 carbon atoms, such as illustratively and preferably ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, dihydroabietylamine, arginine, lysine, ethylenediamine and methylpiperidine.

The term 'alkyl' refers to a straight or branched hydrocarbon chain radical consisting solely of carbon and hydrogen atoms, containing solely of carbon and hydrogen atoms, containing no unsaturation, having from one to eight carbon atoms, and which is attached to the rest of the molecule by a single bond, such as illustratively, methyl, ethyl, n-propyl 1-methylethyl (isopropyl), n-butyl, n-pentyl, and 1,1-dimethylethyl (t-butyl).

The term "alkoxy" denotes an alkyl group as defined herein attached via oxygen linkage to the rest of the molecule. Representative examples of those groups are —OCH$_3$, —OC$_2$H$_5$.

The term "cycloalkyl" denotes a non-aromatic mono or multicyclic ring system of about 3 to 12 carbon atoms such as cyclopropyl, cyclobutyl, cyclopentyl, cyclohexyl and examples of multicyclic cycloalkyl groups include perhydronapththyl, adamantyl and norbornyl groups bridged cyclic group or sprirobicydic groups e.g sprio (4,4) non-2-yl.

The term "halogen" refers to radicals of fluorine, chlorine, bromine and iodine.

A * symbol next to a bond denotes the point of attachment in the molecule.

Throughout this document, for the sake of simplicity, the use of singular language is given preference over plural language, but is generally meant to include the plural language if not otherwise stated. E.g., the expression "A method of treating a disease in a patient, comprising administering to a patient an effective amount of a compound of formula (I)" is meant to include the simultaneous treatment of more than one disease as well as the administration of more than one compound of formula (I).

General Preparative Methods

The particular process to be utilized in the preparation of the compounds used in this embodiment of the invention depends upon the specific compound desired. Such factors as the selection of the specific substituents play a role in the path to be followed in the preparation of the specific compounds of this invention. Those factors are readily recognized by one of ordinary skill in the art.

The compounds of the invention may be prepared by use of known chemical reactions and procedures. Nevertheless, the following general preparative methods are presented to aid the reader in synthesizing the compounds of the present invention, with more detailed particular examples being presented below in the experimental section describing the working examples.

The compounds of the invention can be made according to conventional chemical methods, and/or as disclosed below, from starting materials which are either commercially available or producible according to routine, conventional chemical methods. General methods for the preparation of the compounds are given below, and the preparation of representative compounds is specifically illustrated in examples.

Synthetic transformations that may be employed in the synthesis of compounds of this invention and in the synthesis of intermediates involved in the synthesis of compounds of this invention are known by or accessible to one skilled in the art. Collections of synthetic transformations may be found in compilations, such as:

J. March. *Advanced Organic Chemistry*, 4th ed.; John Wiley: New York (1992)

R. C. Larock. *Comprehensive Organic Transformations*, 2nd ed.; Wiley-VCH: New York (1999)

F. A. Carey; R. J. Sundberg. *Advanced Organic Chemistry*, 2nd ed.; Plenum Press: New York (1984)

T. W. Greene; P. G. M. Wuts. *Protective Groups in Organic Synthesis*, 3rd ed.; John Wiley: New York (1999)

L. S. Hegedus. *Transition Metals in the Synthesis of Complex Organic Molecules*, 2nd ed.; University Science Books: Mill Valley, Calif. (1994)

L. A. Paquette, Ed. *The Encyclopedia of Reagents for Organic Synthesis*; John Wiley: New York (1994)

A. R. Katritzky; O. Meth-Cohn; C. W. Rees, Eds. *Comprehensive Organic Functional Group Transformations*; Pergamon Press: Oxford, UK (1995)

G. Wilkinson; F. G A. Stone; E. W. Abel, Eds. *Comprehensive Organometallic Chemistry*; Pergamon Press: Oxford, UK (1982)

B. M. Trost; I. Fleming. *Comprehensive Organic Synthesis*; Pergamon Press: Oxford, UK (1991)

A. R. Katritzky; C. W. Rees Eds. *Comprehensive Heterocylic Chemistry*, Pergamon Press: Oxford, UK (1984)

A. R. Katritzky; C. W. Rees; E. F. V. Scriven, Eds. *Comprehensive Heterocylic Chemistry II*; Pergamon Press: Oxford, UK (1996)

C. Hansch; P. G. Sammes; J. B. Taylor, Eds. *Comprehensive Medicinal Chemistry*. Pergamon Press: Oxford, UK (1990).

In addition, recurring reviews of synthetic methodology and related topics include *Organic Reactions*; John Wiley: New York; *Organic Syntheses*; John Wiley: New York; *Reagents for Organic Synthesis*: John Wiley: New York; *The Total Synthesis of Natural Products*; John Wiley: New York; *The Organic Chemistry of Drug Synthesis;* John Wiley: New York; *Annual Reports in Organic Synthesis*; Academic Press: San Diego Calif.; and *Methoden der Organischen Chemie* (Houben-Weyl); Thieme: Stuttgart, Germany. Furthermore, databases of synthetic transformations include Chemical Abstracts, which may be searched using either CAS OnLine or SciFinder, *Handbuch der Organischen Chemie* (Beilstein), which may be searched using SpotFire, and REACCS.

The general methods to make compounds of Formula (I) is illustrated in Reaction Schemes 1-4. The route starts with an appropriately substituted 4-nitrobenzoic acid of Formula (II) as shown in Reaction Scheme 1. The acid is converted to an acid chloride, typically with thionyl chloride or oxalyl chloride, and then this is coupled with the magnesium salt of ethylpotassium malonate (III) to afford a β-ketoester of Formula (IV). This compound is condensed with N,N-dimethylformamide dimethyl acetal to afford an α,β-unsaturated ketone of Formula (V) that can then be reacted with 2-aminomalonamide (VI) in the presence of acid (for example acetic acid and trifluoroacetic acid) and heating to form, after cyclization, a pyrrole of Formula (VII). The primary amide group found in the pyrrole of Fomula (VII) can be dehydrated (for example, in the presence of phosphorous oxychloride) to afford a 5-cyanopyrrole of Formula (VIII).

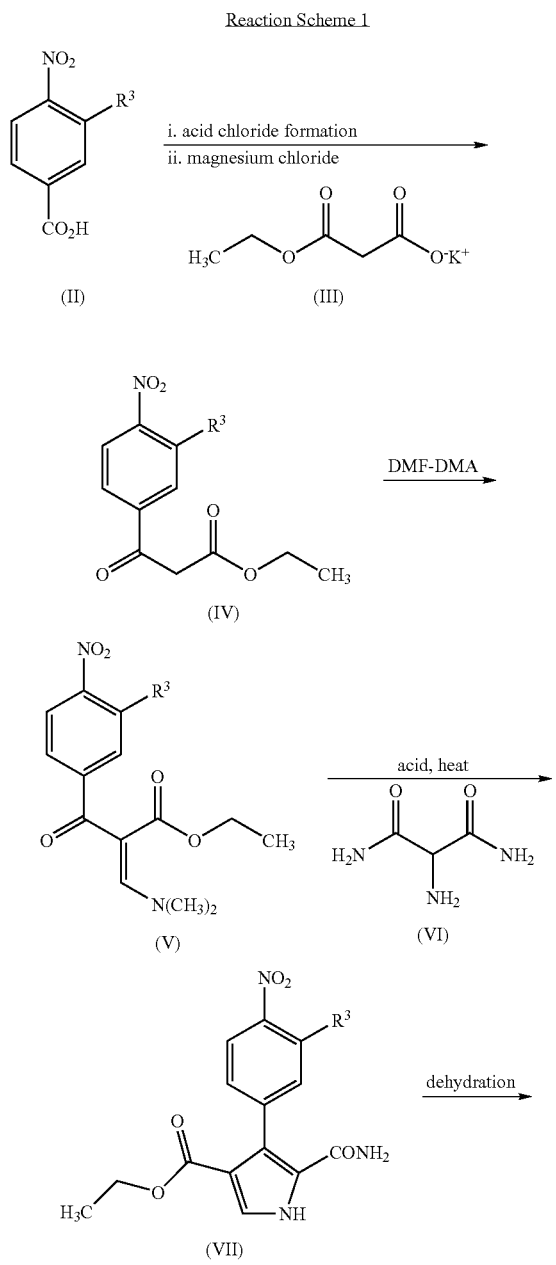

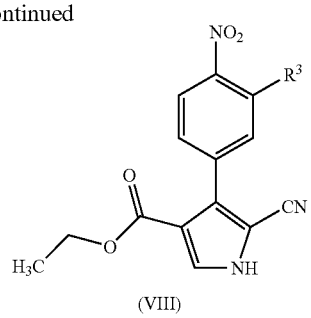

The 5-cyanopyrrole of Formula (VIII) can be advanced as illustrated in Reaction Scheme 2. In one variation, where typically $R^3$ is fluoro, the nitro group of Compound (VIII) can be reduced (for example, with iron in the presence of ammonium chloride and carefully controlled heating) to afford an aniline of Formula (IX). Compound (IX) can then be reacted with an aminating reagent (X) in the presence of a base such as sodium hydride to afford a hydrazine of Formula (XI). Hydrazine (XI) can then be reacted with formamidine acetate and heated to induce cyclization to a pyrrolotriazine of Formula XII.

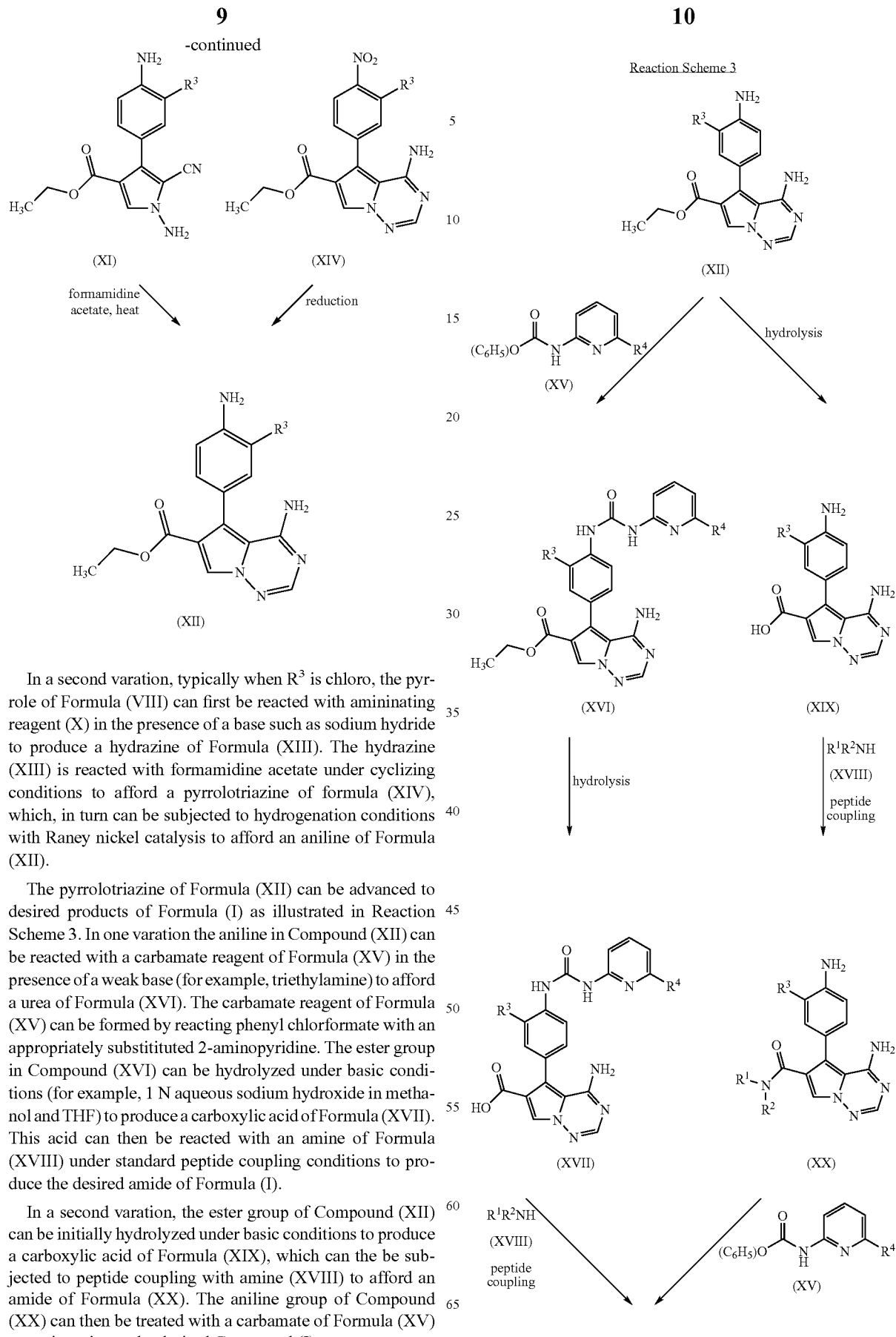

In a second varation, typically when R³ is chloro, the pyrrole of Formula (VIII) can first be reacted with amininating reagent (X) in the presence of a base such as sodium hydride to produce a hydrazine of Formula (XIII). The hydrazine (XIII) is reacted with formamidine acetate under cyclizing conditions to afford a pyrrolotriazine of formula (XIV), which, in turn can be subjected to hydrogenation conditions with Raney nickel catalysis to afford an aniline of Formula (XII).

The pyrrolotriazine of Formula (XII) can be advanced to desired products of Formula (I) as illustrated in Reaction Scheme 3. In one varation the aniline in Compound (XII) can be reacted with a carbamate reagent of Formula (XV) in the presence of a weak base (for example, triethylamine) to afford a urea of Formula (XVI). The carbamate reagent of Formula (XV) can be formed by reacting phenyl chlorformate with an appropriately substitituted 2-aminopyridine. The ester group in Compound (XVI) can be hydrolyzed under basic conditions (for example, 1 N aqueous sodium hydroxide in methanol and THF) to produce a carboxylic acid of Formula (XVII). This acid can then be reacted with an amine of Formula (XVIII) under standard peptide coupling conditions to produce the desired amide of Formula (I).

In a second varation, the ester group of Compound (XII) can be initially hydrolyzed under basic conditions to produce a carboxylic acid of Formula (XIX), which can the be subjected to peptide coupling with amine (XVIII) to afford an amide of Formula (XX). The aniline group of Compound (XX) can then be treated with a carbamate of Formula (XV) to again arrive at the desired Compound (I).

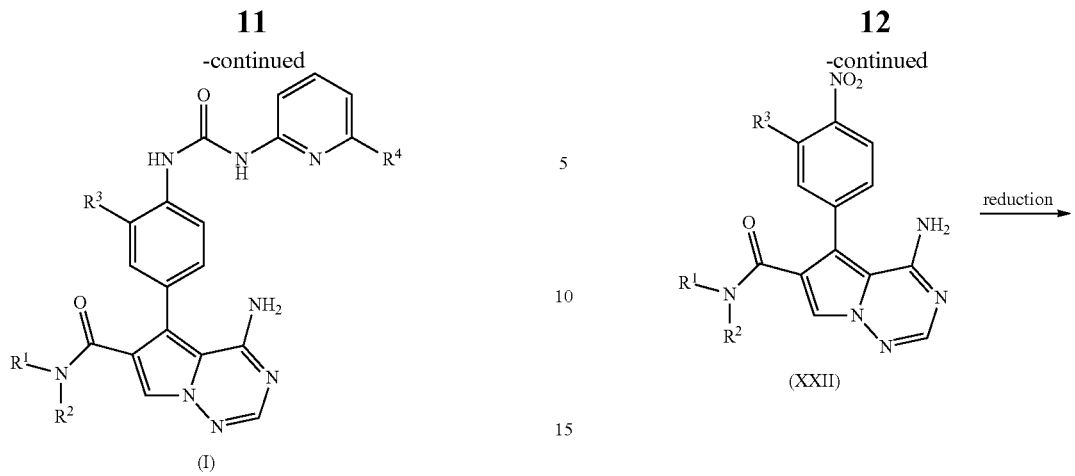

(I)

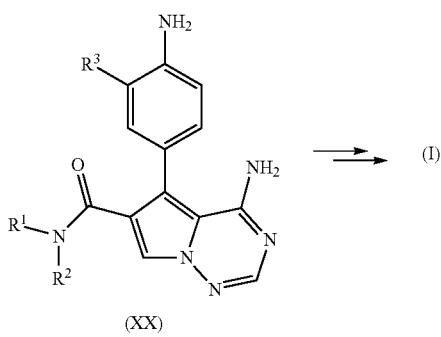

(XXII)

An additional variation to the routes described above that involves a different sequence of reactions is described in Reaction Scheme 4. In this sequence an ester of Formula (XIV), where typically R³ is chloro, is hydrolyzed under standard basic conditions to afford a carboxylic acid of Formula (XXI). The acid (XXI) is subjected to peptide coupling conditions with amine (XVIII) to afford an amide of Formula (XXII). The nitro group in Compound (XXII) can be reduced (for example, by hydrogenation with Raney nickel catalysis) to afford an aniline of Formula (XX). This compound can then undergo urea formation as described in Reaction Scheme 3 to afford the desired compound of Formula (I).

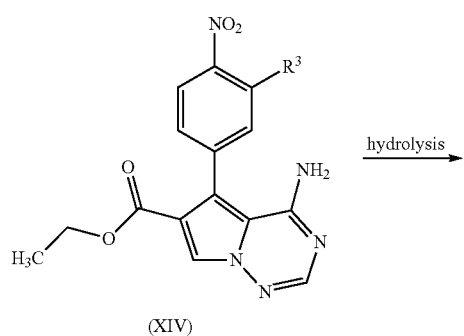

(XX)

Reaction Scheme 4

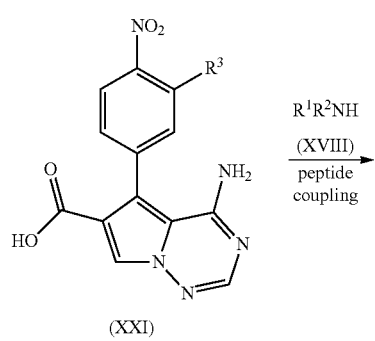

(XIV)

The free base of Formula (I) may also be converted to its corresponding conjugate salt of Formula (Ia) as shown in Reaction Scheme 5. Compounds of Formula (I) are reacted with acids of Formula (XXIII) in solvents such as THF, acetonitrile, or a combination of these and water to afford conjugate salts of Formula (Ia). Acid (XXIII) may be mineral acids such as hydrochloric acid or organic acids such as methane sulfonic acid or oxalic acid. The number of equivalents of Acid (XXIII) may be varied and the stoichiometry of the resulting Conjugate Salt (Ia) is dependent upon the specific Acid (XXIII) used. These Conjugate Salts (Ia) may offer improved dissolution kinetics and oral exposure relative to the free base of Formula (I).

Reaction Scheme 5

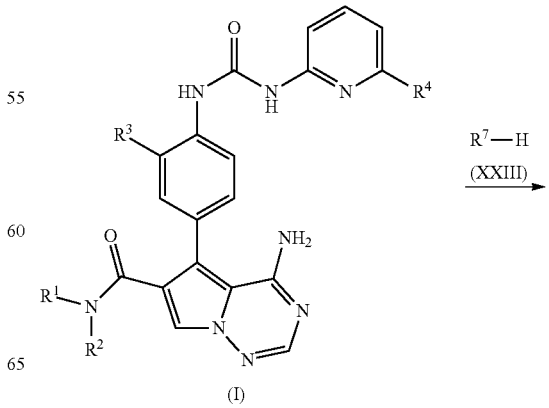

(I)

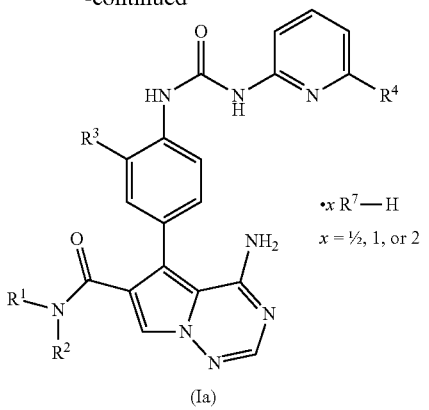

(Ia)

Pharmaceutical Compositions of the Compounds of the Invention

This invention also relates to pharmaceutical compositions containing one or more compounds of the present invention. These compositions can be utilized to achieve the desired pharmacological effect by administration to a patient in need thereof. A patient, for the purpose of this invention, is a mammal, including a human, in need of treatment for the particular condition or disease. Therefore, the present invention includes pharmaceutical compositions that are comprised of a pharmaceutically acceptable carrier and a pharmaceutically effective amount of a compound, or salt thereof, of the present invention. A pharmaceutically acceptable carrier is preferably a carrier that is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is preferably that amount which produces a result or exerts an influence on the particular condition being treated. The compounds of the present invention can be administered with pharmaceutically-acceptable carriers well known in the art using any effective conventional dosage unit forms, including immediate, slow and timed release preparations, orally, parenterally, topically, nasally, ophthalmically, optically, sublingually, rectally, or vaginally.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard-or soft-shelled gelatin type containing, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatin, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, coloring agents, and flavoring agents such as peppermint, oil of wintergreen, or cherry flavoring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavoring and coloring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agent.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavoring and coloring agents.

The compounds of this invention may also be administered parenterally, that is, subcutaneously, intravenously, intraocularly, intrasynovially, intramuscularly, or interperitoneally, as injectable dosages of the compound in preferably a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate.

Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethylcellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono-or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, issued Jun. 11, 1991, incorporated herein by reference). Such patches may be constructed for continuous, pulsatile, or on demand delivery of pharmaceutical agents.

Controlled release formulations for parenteral administration include liposomal, polymeric microsphere and polymeric gel formulations that are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized. Such ingredients and procedures include those described in the following references, each of which is incorporated herein by reference: Powell, M. F. et al, "Compendium of Excipients for Parenteral Formulations" *PDA Journal of Pharmaceutical Science & Technology* 1998, 52(5), 238-311; Strickley, R. G "Parenteral Formulations of Small Molecule Therapeutics Marketed in the United States (1999)-Part-1" *PDA Journal of Pharmaceutical Science & Technology* 1999, 53(6), 324-349; and Nema, S. et al, "Excipients and Their Use in Injectable Products" *PDA Journal of Pharmaceutical Science & Technology* 1997, 51(4), 166-171.

Commonly used pharmaceutical ingredients that can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

aerosol propellants (examples include but are not limited to carbon dioxide, $CCl_2F_2$, $F_2ClC-CClF_2$ and $CClF_3$)

air displacement agents (examples include but are not limited to nitrogen and argon);

antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate)

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection)

chelating agents (examples include but are not limited to edetate disodium and edetic acid)

colorants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate)

flavorants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to arachis oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono-or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas)

plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures));

surfactants (examples include but are not limited to benzalkonium chloride, nonoxynol 10, oxtoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, cross-linked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide);

tablet polishing agents (examples include but are not limited to carnuba wax and white wax);

thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithins, sorbitol monooleate, polyoxyethylene sorbitol monooleate, and polyoxyethylene stearate).

Pharmaceutical compositions according to the present invention can be illustrated as follows:

Sterile IV Solution: A 5 mg/mL solution of the desired compound of this invention can be made using sterile, injectable water, and the pH is adjusted if necessary. The solution is diluted for administration to 1-2 mg/mL with sterile 5% dextrose and is administered as an IV infusion over about 60 minutes.

Lyophilized powder for IV administration: A sterile preparation can be prepared with (i) 100-1000 mg of the desired compound of this invention as a lypholized powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.2-0.4 mg/mL, and is administered either IV bolus or by IV infusion over 15-60 minutes.

Intramuscular suspension: The following solution or suspension can be prepared, for intramuscular injection:

50 mg/mL of the desired, water-insoluble compound of this invention 5 mg/mL sodium carboxymethylcellulose 4 mg/mL TWEEN 80

9 mg/mL sodium chloride 9 mg/mL benzyl alcohol

Hard Shell Capsules: A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules: A mixture of active ingredient in a digestible oil such as soybean oil, cottonseed oil or olive oil is prepared and injected by means of a positive displacement pump into molten gelatin to form soft gelatin capsules containing 100 mg of the active ingredient The capsules are washed and dried. The active ingredient can be dissolved in a mixture of polyethylene glycol, glycerin and sorbitol to prepare a water miscible medicine mix.

Tablets: A large number of tablets are prepared by conventional procedures so that the dosage unit is 100 mg of active ingredient 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules: These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Method of Treating Disorders

The present invention relates to a method for using the compounds of the present invention and compositions thereof, to treat mammalian disorders, in particular hyperproliferative disorders. Compounds can be utilized to inhibit, block, reduce, decrease, etc., cell proliferation and/or cell division, and/or produce apoptosis. This method comprises administering to a mammal in need thereof, including a human, an amount of a compound of this invention, or a pharmaceutically acceptable salt, isomer, polymorph, metabolite, hydrate, solvate or ester thereof; etc. which is effective to treat the disorder. Hyper-proliferative disorders include but are not limited, e.g., psoriasis, keloids, and other hyperplasias affecting the skin, benign prostate hyperplasia (BPH), solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallbladder, gastric, pancreatic, rectal, small-intestine, and salivary gland cancers.

Tumors of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell. Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

The term "treating" or "treatment" as stated throughout this document is used conventionally, e.g., the management or care of a subject for the purpose of combating, alleviating, reducing, relieving, improving the condition of, etc., of a disease or disorder, such as a carcinoma.

Additional Uses of Aurora Kinases in the Treatment of Chemoresistance

In addition to the fundamental role Aurora kinases play in cell cycle regulation, increasing interest exists in examining their use in chemoresistance. In ovarian cancer, for example, chemoresistant recurrence is a significant clinical problem and secondline therapies have limited efficacy; therefore, the potential clinical role for Aurora kinase manipulation in reversing drug resistance may be useful clinically.

Lines of evidence demonstrate a relationship between Aurora kinase expression/activity and resistance to chemotherapy. For example, cell lines stably over-expressing Aurora-A kinase were shown to be more resistant to taxane-induced apoptosis (Anand S, et al. *Cancer Cell* 2003; 3:51-62). Patients with breast tumors with high Aurora-A mRNA levels exhibited a lower response rate to Docetaxel treatment than patients with low Aurora-A mRNA breast tumors—41% versus 71% (Noguchi S. et al. *Cancer Sci* 2006; 97:813-20). And, down-regulation of Aurora-A kinase in pancreatic cancer cell lines using small interfering RNA-based targeting resulted in increased sensitivity to paclitaxel (Hata T. et al. *Cancer Res* 2005; 65:2899-905).

For the reasons discussed above, the therapeutic combination of Aurora kinase inhibitors administered with standard chemotherapeutic agents, such as but not limited to taxanes (paclitaxel, docetaxel) should be effective in reducing drug resistance to those chemotherapeutic agents.

Dose and Administration

Based upon standard laboratory techniques known to evaluate compounds useful for the treatment of hyper-proliferative disorders and angiogenic disorders, by standard toxicity tests and by standard pharmacological assays for the determination of treatment of the conditions identified above in mammals, and by comparison of these results with the results of known medicaments that are used to treat these condiions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, . The desired mode of treatment and number of doses of a compound of the present invention or a pharmaceutically acceptable salt or ester or composition thereof can be ascertained by those skilled in the art using conventional treatment tests.

Combination Therapies

The compounds and compositions of this invention can be administered as the sole pharmaceutical agent or in combination with one or more further active pharmaceutical agents where the combination causes no unacceptable adverse effects. For example, the compounds and compositions of this invention can be combined with known anti-hyper-proliferative or other indication agents, and the like, as well as with admixtures and combinations thereof.

The further active agent can be aldesleukin, alendronic acid, alfaferone, alitretinoin, allopurinol, aloprrn, aloxi, altretamine, aminoglutethimide, amifostine, amrubicin, amsacrine, anastrozole, anzmet, aranesp, arglabin, arsenic trioxide, aromasin, 5-azacytidine, azathioprine, BCG or tice BCG, bestatin, betamethasone acetate, betamethasone sodium phosphate, bexarotene, bleomycin sulfate, broxuridine, bortezomib, busulfan, calcitonin, campath, capecitabine, carboplatin, casodex, cefesone, celmoleukin, cerubidine, chlorambucil, cisplatin, cladribine, cladribine, clodronic acid, cyclophosphamide, cytarabine, dacarbazine, dactinomycin, DaunoXome, decadron, decadron phosphate, delestrogen, denileukin diftitox, depomedrol, deslorelin, dexrazoxane, diethylstilbestrol, diflucan, docetaxel, doxifluridine, doxorubicin, dronabinol, DW-166HC, eligard, elitek, ellence, emend, epirubicin, epoetin alfa, epogen, eptaplatin, ergamisol, estrace, estradiol, estramustine phosphate sodium, ethinyl estradiol, ethyol, etidronic acid, etopophos, etoposide, fadrozole, farston, filgrastim, finasteride, fligrastim, floxuridine, fluconazole, fludarabine, 5-fluorodeoxyuridine monophosphate, 5-fluorouracil (5-FU), fluoxymesterone, flutamide, formestane, fosteabine, fotemustine, fulvestrant, gammagard, gemcitabine, gemtuzumab, gleevec, gliadel, goserelin, granisetron HCl, histrelin, hycamtin, hydrocortone, eyrthro-hydroxynonyladenine, hydroxyurea, ibritumomab tiuxetan, idarubicin, ifosfamide, interferon alpha, interferon-alpha 2, interferon alfa-2α, interferon alfa-2B, interferon alfa-n1, interferon alfa-n3, interferon beta, interferon gamma-1α, interleukin-2, intron A, iressa, irinotecan, kytril, lentinan sulphate, letrozole, leucovorin, leuprolide, leuprolide acetate, levamisole, levofolinic acid calcium salt, levothroid, levoxyl, lomustine, lonidamine, marinol, mechlorethamine, mecobalamin, medroxyprogesterone acetate, megestrol acetate, melphalan, menest, 6-mercaptopurine, Mesna, methotrexate, metvix, miltefosine, minocycline, mitomycin C, mitotane, mitoxantrone, Modrenal, Myocet, nedaplatin, neulasta, neumega, neupogen, nilutamide, nolvadex, NSC-631570, OCT-43, octreotide, ondansetron HCI, oraprcd, oxaliplatin, paclitaxel, pediapred, pegaspargase, Pegasys, pentostatin, picibanil, pilocarpine HCl, pirarubicin, plicamycin, porfimer sodium, prednimustine, prednisolone, prednisone, premarin, procarbazine, procrit, raltitrexed, rebif, rhenium-186 etidronate, rituximab, roferon-A, romurtide, salagen, sandostatin, sargramostim, semustine, sizofiran, sobuzoxane, solu-medrol, sparfosic acid, stem-cell therapy, streptozocin, strontium-89 chloride, synthroid, tamoxifen, tamsulosin, tasonermin, tastolactone, taxotere, teceleukin, temozolomide, teniposide, testosterone propionate, testred, thioguanine, thiotepa, thyrotropin, tiludronic acid, topotecan, toremifene, tositumomab, trastuzumab, treosulfan, tretinoin, trexall, trimethylmelamine, trimetrexate, triptorelin acetate, triptorelin pamoate, UFT, uridine, valrubicin, vesnarinone, vinblastine, vincristine, vindesine, vinorelbine, virulizin, zinecard, zinostatin stimalamer, zofran, ABI-007, acolbifene, actimmune, affinitak, aminopterin, arzoxifene, asoprisnil, atamestane, atrasentan, BAY 43-9006 (sorafenib), avastin, CCI-779, CDC-501, celebrex, cetuximab, crisnatol, cyproterone acetate, decitabine, DN-101, doxorubicin-MTC, dSLIM, dutasteride, edotecarin, eflornithine, exatecan, fenretinide, histamine dihydrochloride, histrelin hydrogel implant, holmium-166 DOTMP, ibandronic acid, interferon gamma, intron-PEG, ixabepilone, keyhole limpet hemocyanin, L-651582, lanreotide, lasofoxifene, libra, lonafarnib, miproxifene, minodronate, MS-209, liposomal MTP-PE, MX-6, nafarelin, nemorubicin, neovastat, nolatrexed, oblimersen, onco-TCS, osidem, paclitaxel polyglutamate, pamidronate disodium, PN-401, QS-21, quazepam, R-1549, raloxifene, ranpirnase, 13-cis -retinoic acid, satraplatin, seocalcitol, T-138067, tarceva, taxoprexin, thymosin alpha 1, tiazofurine, tipifarnib, tirapazamine, TLK-286, toremifene, TransMID-107R, valspodar, vapreotide, vatalanib, verteporfin, vinflunine, Z-100, zoledronic acid or combinations thereof.

Optional anti-hyper-proliferative agents which can be used as a further active agent include but are not limited to compounds listed on the cancer chemotherapy drug regimens in the 11th Edition of the Merck Index, (1996), which is hereby incorporated by reference, such as asparaginase, bleomycin, carboplatin, carmustine, chlorambucil, cisplatin, colaspase, cyclophosphamide, cytarabine, dacarbazine, dactinomycin, daunorubicin, doxorubicin (adriamycine), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, and vindesine.

Other anti-hyper-proliferative agents suitable for use as a further active agent include but are not limited to those compounds acknowledged to be used in the treatment of neoplastic diseases in Goodman and Gilman's The Pharmacological Basis of Therapeutics (Ninth Edition), editor Molinoff et al., publ. by McGraw-Hill, pages 1225-1287, (1996), which is hereby incorporated by reference, such as aminoglutethimide, L-asparaginase, azathioprine, 5-azacytidine cladribine, busulfan, diethylstilbestrol, 2',2'-difluorodeoxycytidine, docetaxel, erythrohydroxynonyl adenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, teniposide, testosterone propionate, thiotepa, trimethylmelamine, uridine, and vinorelbine.

Other anti-hyper-proliferative agents suitable for use as a further active agent with a compound or composition of the invention include but are not limited to other anti-cancer agents such as epothilone and its derivatives, irinotecan, raloxifen and topotecan.

EXAMPLES

Abbreviations and Acronyms

A comprehensive list of the abbreviations used by organic chemists of ordinary skill in the art appears in The ACS Style Guide (third edition) or the Guidelines for Authors for the *Journal of Organic Chemistry*. The abbreviations contained in said lists, and all abbreviations utilized by organic chemists of ordinary skill in the art are hereby incorporated by reference. For purposes of this invention, the chemical elements are identified in accordance with the Periodic Table of the Elements, CAS version, Handbook of Chemistry and Physics, 67th Ed., 1986-87.

More specifically, when the following abbreviations are used throughout this disclosure, they have the following meanings:

atm atmosphere
br s broad singlet
C Celsius
Celite diatomaceous earth filter agent ®Celite Corp.
d doublet
dd doublet of doublets
DMF N,N-dimethylformamide
DMF-DMA N,N-dimethylformamide dimethyl acetal
DMSO dimethylsulfoxide
ES-MS electrospray mass spectroscopy
g gram
h hour, hours
$^1$H NMR proton nuclear magnetic resonance
HPLC high performance liquid chromatography
J coupling constant (NMR spectroscopy)
L liter
M mol L$^{-1}$ (molar)
m multiplet
MHz megahertz
min minute, minutes
mL milliliter
□M micromolar
mol mole
MS mass spectrum, mass spectrometry
m/z mass-to-charge ratio
N equivalents L$^{-1}$ (normal)
NMR Nuclear Magentic Resonance
pH negative logarithm of hydrogen ion concentration
q quartet
RT retention time (HPLC)
rt room temperature
s singlet
t triplet
THF tetrahydrofuran The percentage yields reported in the following examples are based on the starting component that was used in the lowest molar amount. Air and moisture sensitive liquids and solutions were transferred via syringe or cannula, and introduced into reaction vessels through rubber septa. Commercial grade reagents and solvents were used without further purification. The term "concentrated under reduced pressure" refers to use of a Buchi rotary evaporator at approximately 15 mm of Hg. All temperatures are reported uncorrected in degrees Celsius (° C.). Thin layer chromatography (TLC) was performed on pre-coated glass-backed silica gel 60 A F-254 250 μm plates.

The structures of compounds of this invention were confirmed using one or more of the following procedures.

NMR

NMR spectra were acquired for each compound and were consistent with the structures shown.

Routine one-dimensional NMR spectroscopy was performed on either 300 or 400 MHz Varian® Mercury-plus spectrometers. The samples were dissolved in deuterated solvents. Chemical shifts were recorded on the ppm scale and were referenced to the appropriate solvent signals, such as 2.49 ppm for DMSO-d6, 1.93 ppm for CD3CN, 3.30 ppm for CD3OD, 5.32 ppm for CD2Cl2 and 7.26 ppm for CDCl3 for 1H spectra.

GC/MS

Electron impact mass spectra (EI-MS) were obtained with a Hewlett Packard 5973 mass spectrometer equipped Hewlett Packard 6890 Gas Chromatograph with a J & W HP-5 column (0.25 uM coating; 30 m×0.32 mm). The ion source was maintained at 250° C. and spectra were scanned from 50-550 amu at 0.34 sec per scan.

LC/MS

Unless otherwise noted, all retention times are obtained from the LC/MS and correspond to the molecular ion. High pressure liquid chromatography-electrospray mass spectra (LC/MS) were obtained using one of the following:

Method A (LCQ)

Hewlett-Packard 1100 HPLC equipped with a quaternary pump, a variable wavelength detector set at 254 nm, a Waters Sunfire C18 column (2.1×30 mm, 3.5 μm), a Gilson autosampler and a Finnigan LCQ ion trap mass spectrometer with electrospray ionization. Spectra were scanned from 120-1200 amu using a variable ion time according to the number of ions in the source. The eluents were A: 2% acetonitrile in water with 0.02% TFA, and B: 2% water in acetonirile with 0.018% TFA. Gradient elution from 10% B to 95% B over 3.5 minutes at a flow rate of 1.0 mL/min was used with an initial hold of 0.5 minutes and a final hold at 95% B of 0.5 minutes. Total run time was 6.5 minutes.

Method B (LCQ5)

Agilent 1100 HPLC system. The Agilent 1100 HPLC system was equipped with an Agilent 1100 autosampler, quaternary pump, a variable wavelength detector set at 254 nm. The HPLC column used was a Waters Sunfire C-18 column (2.1× 30 mm, 3.5 μm). The HPLC eluent was directly coupled without splitting to a Finnigan LCQ DECA ion trap mass spectrometer with electrospray ionization. Spectra were scanned from 140-1200 amu using a variable ion time according to the number of ions in the source using positive ion mode. The eluents were A: 2% acetonitrile in water with 0.02% TFA, and B: 2% water in acetonirile with 0.02% TFA. Gradient elution from 10% B to 90% B over 3.0 minutes at a flow rate of 1.0 mL/min was used with an initial hold of 1.0 minutes and a final hold at 95% B of 1.0 minutes. Total run time was 7.0 minutes.

Method C (LTQ)

Agilent 1100 HPLC system. The Agilent 1100 HPLC system was equipped with an Agilent 1100 autosampler, quaternary pump, and a diode array. The HPLC column used was a Waters Sunfire C18 column (2.1×30 mm, 3.5 μm). The HPLC eluent was directly coupled with a 1:4 split to a Finnigan LTQ ion trap mass spectrometer with electrospray ionization. Spectra were scanned from 50-800 amu using a variable ion time according to the number of ions in the source using positive or negative ion mode. The eluents were A: water with 0.1 formic acid, and B: acetonitrile with 0.1% formic acid. Gradient elution from 10% B to 90% B over 3.0 minutes at a flowrate of 1.0 mL/min was used with an initial hold of 2.0 minutes and a final hold at 95% B of 1.0 minutes. Total run time was 8.0 minutes.

Preparative HPLC:

Preparative HPLC was carried out in reversed phase mode, typically using a Gilson HPLC system equipped with two Gilson 322 pumps, a Gilson 215 Autosampler, a Gilson diode array detector, and a C-18 column (e.g. YMC Pro 20×150 mm, 120 A). Gradient elution was used with solvent A as water with 0.1% TFA, and solvent B as acetonitrile with 0.1% TFA. Following injection onto the column as a solution, the compound was typically eluted with a mixed solvent gradient, such as 10-90% Solvent B in Solvent A over 15 minutes with flow rate of 25 mL/min. The fraction(s) containing the desired product were collected by UV monitoring at 254 or 220 nm.

Preparative MPLC:

Preparative medium pressure liquid chromatography (MPLC) was carried out by standard silica gel "flash chromatography' techniques (e.g., Still, W. C. et al. *J. Org. Chem.* 1978, 43, 2923-5), or by using silica gel cartridges and devices such as the Biotage Flash systems. A variety of eluting solvents were used, as described in the experimental protocols.

In order that this invention may be better understood, the following examples are set forth. These examples are for the purpose of illustration only, and are not to be construed as limiting the scope of the invention in any manner. All publications mentioned herein are incorporated by reference in their entirety.

INTERMEDIATES

Intermediate A

Preparation of ethyl 3-(3-fluoro-4-nitrophenyl)-3-oxopropanoate

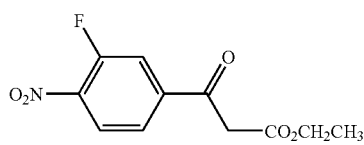

Thionyl chloride (96.4 g, 810 mmol) was added dropwise (30 min) to a solution of 3-fluoro-4-nitrobenzoic acid (100 g, 540 mmol) in 1,2-dichloroethane (500 mL) and DMF (1 mL). The reaction was warmed (70° C.) for 4 h and cooled to rt. Volatiles were evaporated under reduced pressure to afford the intermediate acid choride. This material was dissolved in THF (500 mL) and then filtered to remove residual solids.

Magnesium chloride was added to a cooled (10° C.) suspension of ethylpotassium malonate (276 g, 1620 mmol) and triethylamine (164 g, 1620 mmol) in THF (1500 mL). This mixture was stirred vigorously (overhead stirrer) for 12 h at rt, and then cooled (0° C.). The filtered acid chloride solution in THF was added dropwise (30 min). The reaction was allowed to warm to rt, stirred for 12 h and then cooled (10 ° C.). 4 N hydrochloric acid (1 L) was added slowly, while maintaining the reaction temperature below 20° C. The quenched reaction was diluted with water (1 L) and then extracted with ethyl acetate (3×1 L). The combined organic extracts were washed with saturated aqueous sodium bicarbonate solution (2×1 L), water (1 L) and brine (1 L), dried over sodium sulfate, and evaporated under reduced pressure to afford the desired product (134 g, 97%) as a mixture of tautomers. $^1$H-NMR (300 MHz, DMSO-$d_6$) Tautomer 1: δ 12.24 (s, 1H), 7.85-8.32 (m, 3H), 6.22 (s, 3H), 4.25 (q, J=7.0 Hz, 2H), 1.26, (t, J=7.0 Hz, 3H); Tautomer 2: δ 7.90-8.38 (m, 3H), 4.30 (s, 2H), 4.11 (q, J=7.1 Hz, 2H), 1.17 (t, J=7.1 Hz, 3H); ES-MS m/z 254.1 (M−H)$^−$; HPLC RT (Method C) 3.14 min.

Intermediate B

Preparation of ethyl 2-(3-fluoro-4-nitrobenzoyl)-3-(dimethylamino)acrylate

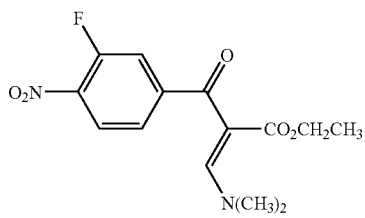

N,N-Dimethylformamide dimethyl acetal (100 g, 810 mmol) was added dropwise (10 min) to a cooled (0° C.) solution of Intermediate A (138 g, 540 mmol) in toluene (540 mL). The reaction was warmed (50° C.) for 2.5 h and then the volatiles were evaporated under reduced pressure to afford the desired product (167 g, 100%), which was sufficiently pure (>95% by NMR) to proceed without futher purification. $^1$H NMR (300 MHz, DMSO-$d_6$) δ 8.24-8.29 (m, 1H), 7.92 (s, 1H), 7.60-7.74 (m, 1H), 7.58-7.62 (m, 1H), 3.97 (q, J=7.0 Hz, 2H), 3.44 (s, 3H), 2.81 (s, 3H), 0.99 (t, J=7.0 Hz, 3H); ES-MS m/z 310.9 (MH)$^+$; HPLC RT (Method B) 2.87 min.

Intermediate C

Preparation of ethyl 5-carbamoyl-4-(3-chloro-4-nitrophenyl)-1H-pyrrole-3-carboxylate

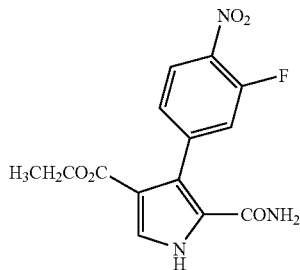

2-Aminomalonamide (36.5 g, 312 mmol) was added to a stirred solution of Intermediate B (74.4 g, 240 mmol) in acetic acid (300 mL). The suspension was warmed (80° C.) for 2 h and then the acetic acid was evaporated under reduced pressure. The residue was dissolved in trifluoroacetic acid (300 mL) and the resulting solution was warmed (60° C.) for 4 h. The trifluoroacetic acid was evaporated under reduced pressure and the solid was washed with cold ethanol (2×50 mL)

and diethyl ether (3×50 mL) to afford the desired product (58.8 g, 76%). ¹H NMR (300 MHz, DMSO-d₆) δ 12.35 (s, 1H), 8.12 (dd, J=8.3, 8.3 Hz, 1H), 7.63 (s, 1H), 7.52 (d, J=12.3 Hz, 1H), 7.25-7.50 (m, 2H), 6.74 (s, 1H), 4.06 (q, J=7.1 Hz, 2H), 1.11 (t, J=7.1 Hz, 3H); ES-MS m/z 322.0 (MH)⁺; HPLC RT (Method B) 2.79 min.

Intermediate D

Preparation of ethyl 5-cyano-4-(3-fluoro-4-nitrophenyl)-1H-pyrrole-3-carboxylate

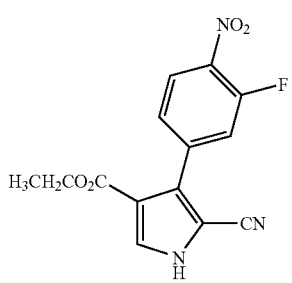

Phoshorous oxychloride (87.0 g, 565 mmol) was added to a suspension of Intermediate C (121 g, 377 mmol) in toluene (750 mL) equipped with an overhead stirrer. The suspension was heated (80° C.) and stirred for 6 h with the periodic addition of toluene (200 mL total) to rinse solids from the sides of the flask, and then the volatiles were evaporated under reduced pressure. The residue was suspended in toluene (500 mL) and this was evaporated to remove remaining phosphorous oxychloride (this operation was done two times). Cold water (750 mL) was added and the mixture was adjusted to pH 8 using 5 N aqueous sodium hydroxide. The solid was collected by filtration and dried to afford the desired product (110 g, 96%); ¹H NMR (300 MHz, DMSO-d₆) δ 12.90 (s, 1H), 7.75 (s, 1H), 7.07 (dd, J=8.2, 8.2 Hz, 1H), 7.77 (dd, J=12.4, 1.8 Hz, 1H), 7.51-7.62 (m, 1H), 4.16 (q, J=7.1 Hz, 2H), 1.19 (t, J=7.1 Hz, 3H); ES-MS m/z 304.1 (MH)⁺; HPLC RT (Method A) 3.19 min.

Intermediate E

Preparation of ethyl 4-(4-amino-3-fluorophenyl)-5-cyano-1H-pyrrole-3-carboxylate

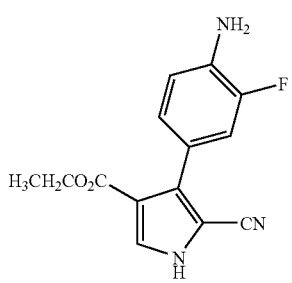

Iron (Alrich cat#20930-9, 24.9 g, 445 mmol) and ammonium chloride (4.80 g, 89.7 mmol) were added to a suspension of Intermediate D (45.0 g, 148 mmol) in ethanol (540 mL) and water (180 mL) equipped with an overhead stirrer. The reaction was warmed (70° C.) for 2 h, and then cooled to rt. The mixture was diluted with methanol (500 mL) and then filtered through a well-packed pad of Celite. The filter cake was throroughly rinsed with methanol (1 L) and acetonitrile (2 L) and the combined filtrate was evaporated. The residue was dissolved in ethyl acetate (1.5 L) then washed with water (500 mL) and brine (500 mL). The organic layer was dried over sodium sulfate and evaporated under reduced pressure to afford the desired product (38.0 g, 94%) containing trace impurities (<5%). The material was used in the next step without further purification. ¹H NMR (300 MHz, DMSO-d₆) δ 13.36 (s, 1H), 8.25 (dd, J=12.8, 2.0 Hz, 1H), 6.92-6.97 (m, 1H), 6.72-6.79 (m, 1H), 5.35 (s, 2H), 4.10 (q, J=7.0 Hz, 2H), 1.16 (t, J=7.0 Hz, 3H); ES-MS m/z 274.3 (MH)⁺; HPLC RT (Method A) 2.62 min.

Intermediate F

Preparation of ethyl 1-amino-4-(4-amino-3-fluorophenyl)-5-cyano-1H-pyrrole-3-carboxylate

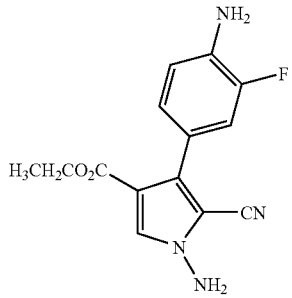

Sodium hydride (60% dispersion in oil, 1.7 g, 43 mmol) was added in portions to a solution of Intermediate E (9.0 g, 33 mmol) in DMF (290 mL). The suspension was stirred for 30 min and then (aminooxy)(diphenyl)phosphine oxide (9.9 g, 43 mmol) was added. The reaction was warmed (60° C.) for 4 h and then cooled to rt. The reaction was quenched by slow addition of water (10 mL) and the solvents were evaporated under reduced pressure. The residue was dissolved in ethyl acetate (500 mL) and the solution was washed with saturated aqueous sodium bicarbonate solution (2×250 mL) and brine (250 mL). The organic layer was dried over sodium sulfate and evaporated. The residue was triturated with diethyl ether to give the desired product (7.8 g, 82%); ¹H NMR (300 MHz, DMSO-d₆) δ 7.57 (s, 1H), 7.05 (dd, J=12.7, 2.0 Hz, 1H), 6.91-6.95 (m, 1H), 6.75 (dd, J=9.5, 8.4 Hz, 1H), 6.57 (s, 2H), 5.36 (s, 2H), 4.09 (q, J=7.0 Hz, 2H), 1.16 (t, J=7.0 Hz, 3H); ES-MS m/z 289.0 (MH)⁺; HPLC RT (Method B) 2.61 min.

Intermediate G

Preparation of ethyl 4-amino-5-(4-amino-3-fluorophenyl)pyrrolo[2,1-f][1,2,4]triazine-6-carboxylate

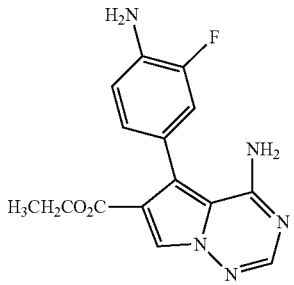

Formamidine acetate (22.4 g, 215 mmol) was added to a suspension of Intermediate F (6.2 g, 21.5 mmol) in n-butanol (100 mL). The reaction was heated (100° C.) for 16 h and then cooled to rt. The solvent was removed under reduced pressure and then ethanol (50 mL) and water (200 mL) were added. The mixture was stirred for 30 min and the resulting precipitate was collected by filtration. The solid was washed with water (2×50 mL) and dried to afford desired product (5.80 g, 85%); $^1$H NMR (300 MHz, DMSO-$d_6$) δ 8.08 (s, 1H), 8.00-8.10 (br s, 1H), 7.90 (s, 1H), 7.03 (dd, J=12.3, 1.9 Hz, 1H), 6.77-6.88 (m, 2H), 5.36 (s, 2H), 5.21-5.31 (br s, 1H), 4.06 (q, J=7.1 Hz, 2H), 1.11 (t, J=7.1 Hz, 3H); ES-MS m/z 316.4 (MH)$^+$; HPLC RT (Method B) 2.39 min.

Intermediate H

Preparation of ethyl 4-amino-5-(3-fluoro-4-{[(6-methylpyridin-2-yl)carbamoyl]amino}phenyl)pyrrolo[2,1-f][1,2,4]triazine-6-carboxylate

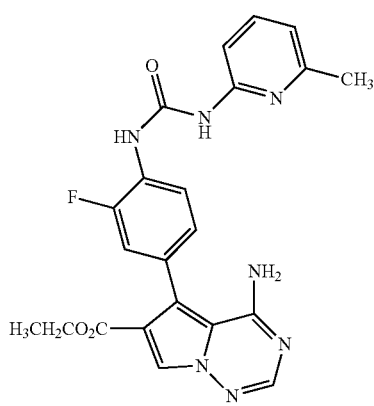

Intermediate G (7.00 g, 22.2 mmol) was added to a solution of phenyl (6-methylpyridin-2-yl)carbamate (10.1 g, 44.4 mmol) and triethylamine (9.3 mL, 66.6 mmol) in DMF (50 mL). The reaction mixture was stirred at rt for 16 h and then diluted with water (300 mL). The mixture was extracted with ethyl acetate (3×100 mL) and the combined organic extracts were washed with water (2×200 mL) and brine (200 mL). The organic layer was dried over sodium sulfate and evaporated. The resulting solid was triturated with diethyl ether to give the desired product (8.8 g, 88%); $^1$H NMR (300 MHz, DMSO-$d_6$) δ 9.94 (s, 1H), 8.36 (dd, J=8.5, 8.5 Hz, 1H), 8.14 (s, 1H), 7.95-8.09 (br s, 1H), 7.94 (s, 1H), 7.66 (dd, J=7.8, 7.8 Hz, 1H), 7.35 (dd, J=11.9, 2.0 Hz, 1H), 7.16 (dd, J=8.5, 1.8 Hz, 1H), 6.95-7.03 (m, 1H), 6.90 (d J=7.4 Hz, 1H), 5.26-3.34 (br s, 1H), 4.08 (q, J=7.2 Hz, 2H), 2.46 (s, 3H), 1.10 (t, J=7.2 Hz, 3H); ES-MS m/z 450.2 (MH)$^+$; HPLC RT (Method A) 2.86 min.

Intermediate I

Preparation of 4-amino-5-(3-fluoro-4-{[(6-methylpyridin-2-yl)carbamoyl]amino}phenyl)pyrrolo[2,1-f][1,2,4]triazine-6-carboxylic acid

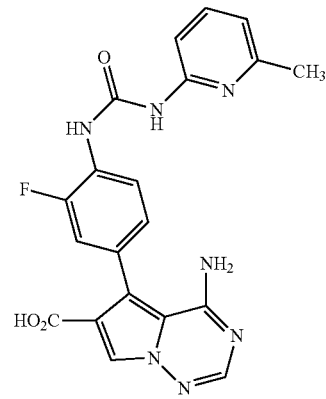

1 N aqueous sodium hydroxide (20 mL, 20 mmol) was added to a suspension of Intermediate H (4.50 g, 10.0 mmol) in THF (35 mL) and ethanol (35 mL). The reaction mixture was heated (65° C.) for 16 h and then cooled to rt. Hydrogen chloride (4 N in 1,4-dioxane, 7.5 mL, 30 mmol) was added and the volatiles were removed under reduced pressure. The residue was washed with water and then triturated with acetone and diethyl ether to give the desired product (3.0 g, 71%); $^1$H NMR (300 MHz, DMSO-$d_6$) δ 12.32-12.49 (br s, 1H), 9.93 (s, 1H), 8.34 (dd, J=8.5, 8.5 Hz, 1H), 8.06 (s, 1H), 7.95-8.03 (br s, 1H), 7.91 (s, 1H), 7.66 (dd, J=7.8, 7.8 Hz, 1H), 7.34 (dd, J=12.0, 1.9 Hz, 1H), 7.15 (dd, J=8.5, 1.8 Hz, 1H), 6.96-7.03 (m, 1H), 6.90 (d J=7.4 Hz, 1H), 5.25-3.34 (br s, 1H), 2.46 (s, 3H); ES-MS m/z 422.3 (MH)$^+$; HPLC RT (Method B) 2.13 min.

Intermediate J

Preparation of 4-amino-5-(4-amino-3-fluorophenyl)pyrrolo[2,1-f][1,2,4]triazine-6-carboxylic acid

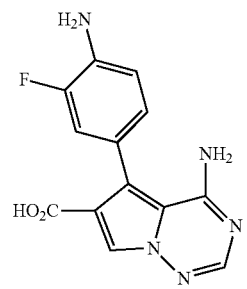

The procedure used for the preparation of Intermedate I was used to prepare the title compound by substituting Intermediate G for Intermediate H. $^1$H NMR (300 MHz, DMSO-$d_6$) δ 12.20-12.30 (br s, 1H), 8.03 (s, 1H), 7.94-8.05 (br s, 1H), 7.89 (s, 1H), 7.02 (dd, J=12.4, 2.0 Hz, 1H), 6.73-6.92 (m, 2H), 5.22-5.47 (br s, 1H), 5.12-5.25 (br s, 1H); ES-MS m/z 288.0 (MH)⁺; HPLC RT (Method A) 1.13 min.

Intermediate K

Preparation of 4-amino-5-(4-amino-3-fluorophenyl)-N-(2,2,2-trifluoroethyl)pyrrolo[2,1-f][1,2,4]triazine-6-carboxamide

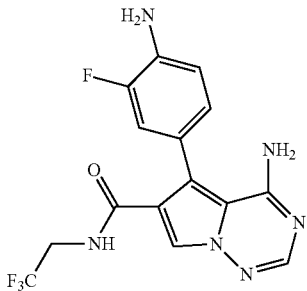

Intermediate J (24.6 g, 85.6 mmol) was added to a mixture of 2,2,2-trifluoro-1-aminoethane (42.4 g, 428 mmol), benzotriazolyloxytris(dimethylamino)phosphonium PF6 (56.8 g, 128 mmol) and 4-methylmorpholine (43.3 g, 428 mmol) in DMF (500 mL). The reaction mixture was stirred at rt for 16 h. The resulting precipitate was isolated by filtration and then washsed with acetone and diethyl ether to give the desired product (22 g, 70%); $^1$H NMR (300 MHz, DMSO-d$_6$) δ 8.37 (dd, J=8.5, 8.5 Hz, 1H), 8.12 (s, 1H), 7.94 (s, 1H), 7.92-8.03 (br s, 1H), 7.89 (s, 1H), 6.99 (dd, J=12.2, 1.8 Hz, 1H), 6.85 (dd, J=12.2, 1.8 Hz, 1H), 6.74-6.6.82 (m, 1H), 5.35 (s, 2H), 5.13-3.22 (br s, 1H), 3.87-4.01 (m, 2H); ES-MS m/z 369.2 (MH)⁺; HPLC RT (Method B) 2.05 min.

Intermediate L

Preparation of 4-amino-5-(4-amino-3-fluorophenyl)-N-tert-butylpyrrolo[2,1-f][1,2,4]triazine-6-carboxamide

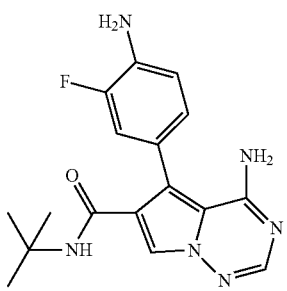

The procedure used for the preparation of Intermedate K was used to prepare the title compound by substituting t-butylamine for 2,2,2-trifluoro-1-aminoethane. $^1$H NMR (300 MHz, DMSO-d$_6$) δ 7.96 (s, 1H), 7.87 (s, 1H), 7.07 (dd, J=12.3, 1.9 Hz, 1H), 6.92 (dd, J=8.1, 1.9 Hz, 1H), 6.81-6.6.89 (m, 1H), 5.44 (s, 2H), 1.16 (s, 9H); ES-MS m/z 343.1 (MH)⁺; HPLC RT (Method A) 2.11 min.

Intermediate M

Preparation of ethyl 3-(3-chloro-4-nitrophenyl)-3-oxopropanoate

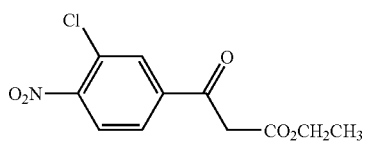

The procedure used for the preparation of Intermedate A was used to prepare the title compound by substituting 3-chloro-4-nitrobenzoic acid for 3-fluoro-4-nitrobenzoic acid. $^1$H-NMR (300 MHz, DMSO-d$_6$) Tautomer 1: δ 12.47 (s, 1H), 8.21 (d, J=1.8 Hz, 1H), 8.16 (d, J=8.6 Hz, 1H), 8.04 (dd, J=8.5, 1.9 Hz, 1H), 6.24 (s, 1H), 4.25 (q, J=7.1 Hz, 2H), 1.26 (t, J=7.1 Hz); Tautomer 2: δ 8.27 (d, J=1.8 Hz, 1H), 8.22 (d, J=6.6 Hz, 1H), 8.09 (dd, J=8.4, 1.9 Hz, 1H), 4.32 (s, 2H), 4.11 (q, J=7.1 Hz, 2H), 1.17 (t, J=7.1 Hz, 3H); ES-MS m/z 270.0 (M−H)⁻; HPLC RT (Method C) 4.80 min.

Intermediate N

Preparation of ethyl 2-(3-chloro-4-nitrobenzoyl)-3-(dimethylamino)acrylate

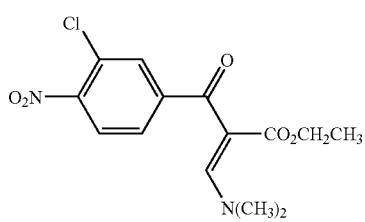

The procedure used for the preparation of Intermedate B was used to prepare the title compound by substituting intermediate M for Intermediate A. $^1$H-NMR (300 MHz, DMSO-d$_6$) δ 8.09 (d, J=8.5 Hz, 1H), 7.83 (s, 1H), 7.77 (s, 1H), 7.65 (dd, J=8.2, 1.7 Hz, 1H), 3.87 (q, J=7.1 Hz, 2H), 3.32 (s, 3H), 2.71 (s, 3H), 0.89 (t, J=7.1 Hz, 3H); ES-MS m/z 326.8 (MH)+; HPLC RT (Method A) 3.00 min.

Intermediate O

Preparation of ethyl 5-carbamoyl-4-(3-chloro-4-nitrophenyl)-1H-pyrrole-3-carboxylate

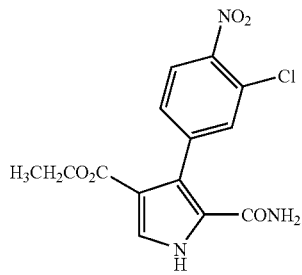

The procedure used for the preparation of Intermedate C was used to prepare the title compound by substituting Intermediate N for Intermediate B. $^1$H-NMR (300 MHz, DMSO-$d_6$) δ 12.25 (s, 1H), 8.00 (d, J=8.5 Hz, 1H), 7.59-7.63 (m, 2H), 7.42 (dd, J=8.5, 1.8 Hz, 1H), 7.25-7.38 (br s, 1H), 6.68-7.79 (br s, 1H), 4.02 (q, J=7.1 Hz, 2H), 1.07 (t, J=7.1 Hz, 3H); ES-MS m/z 337.9 (MH)+; HPLC RT (Method A) 2.89 min.

Intermediate P

Preparation of ethyl 4-(3-chloro-4-nitrophenyl)-5-cyano-1H-pyrrole-3-carboxylate

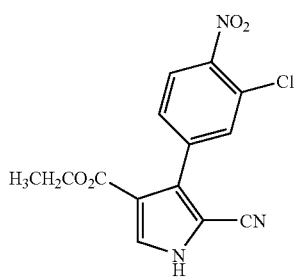

The procedure used for the preparation of Intermedate D was used to prepare the title compound by substituting Intermediate O for Intermediate C. $^1$H-NMR (300 MHz, DMSO-$d_6$) δ 13.30 (s, 1H), 8.14 (d, J=8.4 Hz, 1H), 7.91 (s, 1H), 7.87 (d, J=2.0 Hz, 1H), 7.65 (dd, J=8.4, 1.8 Hz, 1H), 4.12 (q, J=7.1 Hz, 2H), 1.14 (t, J=7.1 Hz, 3H); ES-MS m/z 318.1 (M–H)−; HPLC RT (Method A) 4.88 min.

Intermediate Q

Preparation of ethyl 1-amino-4-(3-chloro-4-nitrophenyl)-5-cyano-1H-pyrrole-3-carboxylate

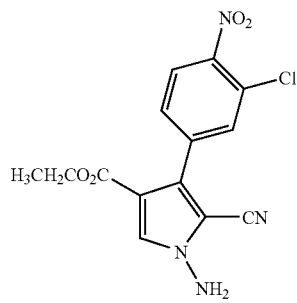

Sodium hydride (60% dispersion in mineral oil, 1.36 g, 33.9 mmol) was added in 3 portions over 15 min to a solution of Intermediate P (8.34 g, 26.1 mmol) in DMF (230 mL). The mixture was stirred at it for 30 min. (Aminooxy)(diphenyl)phosphine oxide (8.51 g, 37.3 mmol) was added in one portion. The mixture was heated (60° C.) overnight. The mixture was cooled to it and diluted with ethyl acetate (500 mL), saturated aqueous sodium bicarbonate solution (250 mL), and water (500 mL). The layers were separated and the aqueous layer was extracted with ethyl acetate (2×500 mL). The combined organic extracts were washed with water and brine, dried over sodium sulfate and concentrated under reduced pressure to give a quantitative yield of crude product, which was used in the next step without purification. $^1$H-NMR (300 MHz, DMSO-$d_6$) δ 8.14 (d, J=8.3 Hz, 1H), 7.85 (d, J=1.7 Hz, 1H), 7.72 (s, 1H), 7.62 (dd, J=8.5, 1.9 Hz, 1H), 6.72 (s, 2H), 4.11 (q, J=7.1 Hz, 2H), 1.14 (t, J=7.1 Hz, 3H); ES-MS m/z 335.1 (MH)+; HPLC RT (Method A) 3.40 min.

Intermediate R

Preparation of ethyl 4-amino-5-(3-chloro-4-nitrophenyl)pyrrolo[2,1-f][1,2,4]triazine-6-carboxylate

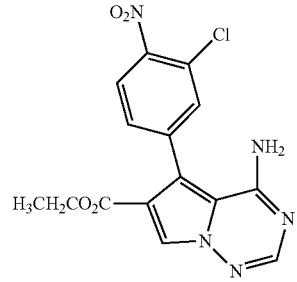

Formamidine acetate (27.1 g, 260 mmol) was added to a solution of Intermediate Q (8.70 g, 26.0 mmol) in n-butanol (120 mL). The reaction was heated (100° C.) for 16 h and then cooled to rt. The solvent was evaporated under reduced pressure. The residue was purified by silica gel chromatography, using a 10-50% gradient of ethyl acetate in hexane as the eluent, to afford the desired product (4.10 g, 44%). $^1$H-NMR (300 MHz, DMSO-d$_6$) δ 8.20 (s, 1H), 8.08 (d, J=8.2 Hz, 1H), 7.97 (s, 1H), 7.79 (d, J=1.8 Hz, 1H), 7.54 (dd, J=1.7, 8.4 Hz, 1H), 4.08 (q, J=7.1 Hz, 2H), 1.09 (t, J=7.1 Hz, 3H); ES-MS m/z 362.1 (MH)$^+$; HPLC RT (Method A) 3.06 min.

Intermediate S

Preparation of ethyl 4-amino-5-(4-amino-3-chlorophenyl)pyrrolo[2,1-f][1,2,4]triazine-6-carboxylate

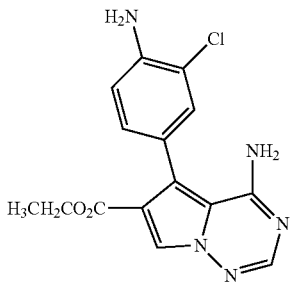

A mixture of Intermediate R (0.74 g, 2.05 mmol), Raney nickel (approximately 300-500 mg) and ethanol (20 mL) was stirred under hydrogen (1 atm) overnight. The suspension was diluted with ethanol (500 mL) and filtered through a pad of Celite using ethanol to rinse. The filtrate was concentrated to dryness under reduced pressure. The residue was purified by HPLC using a gradient of 35 to 60% acetonitrile in water to afford the desired product (0.36 g, 53%). $^1$H-NMR (300 MHz, DMSO-d$_6$) δ 8.11 (s, 1H), 8.00-8.09 (br s, 1H), 7.93 (s, 1H), 7.24 (d, J=2.0 Hz, 1H), 7.04 (dd, J=8.2, 2.0 Hz, 1H), 6.85 (d, J=8.3 Hz, 1H), 5.59 (s, 2H), 5.20-5.30 (br s, 1H), 4.10 (q, J=7.1 Hz, 2H), 1.13 (t, J=7.1 Hz, 3H); ES-MS m/z 332.2 (MH)$^+$; HPLC RT (Method B) 2.64 min.

Intermediate T

Preparation of ethyl 4-amino-5-(3-chloro-4-{[(6-methylpyridin-2-yl)carbamoyl]amino}phenyl)pyrrolo[2,1-f][1,2,4]triazine-6-carboxylate

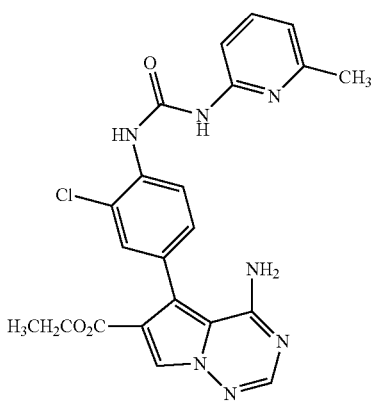

The procedure used for the preparation of Intermedate H was used to prepare the title compound by substituting Intermediate S for Intermediate G. $^1$H-NMR (300 MHz, DMSO-d$_6$) δ 10.03 (s, 1H), 8.43 (d, J=8.5 Hz, 1H), 8.15 (s, 1H), 7.99-8.11 (br s, 1H), 7.94 (s, 1H), 7.62-7.70 (m, 1H), 7.54 (d, J=1.9 Hz, 1H), 7.32 (dd, J=8.6, 1.9 Hz, 1H), 6.91-7.02 (br s, 1H), 6.90 (d, J=7.4 Hz, 1H), 5.37-5.48 (br s, 1H), 4.08 (q, J=7.1 Hz, 2H), 2.47 (s, 3H), 1.11 (t, J=7.1 Hz, 3H); ES-MS m/z 466.2 (MH)$^+$; HPLC RT (Method B) 3.13 min.

Intermediate U

Prepration of 4-amino-5-(3-chloro-4-{[6-methylpyridin-2-yl)carbamoyl]amino}phenyl)pyrrolo[2,1-f][1,2,4]triazine-6-carboxylic acid

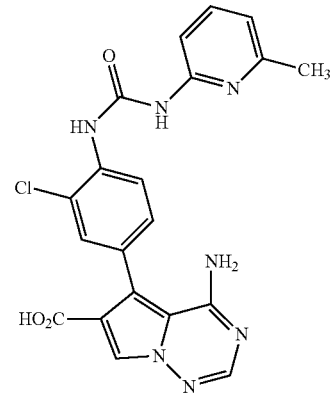

The procedure used for the preparation of Intermedate I was used to prepare the title compound by substituting Intermediate T for Intermediate H. $^1$H-NMR (300 MHz, DMSO-d$_6$) δ 10.03 (s, 1H), 8.41 (d, J=8.6 Hz, 1H), 8.12 (s, 1H), 8.00-8.16 (br s 1H), 7.95 (s, 1H), 7.62-7.70 (m, 1H), 7.53 (d, J=2.1 Hz, 1H), 7.32 (dd, J=8.5, 2.0 Hz, 1H), 6.92-7.04 (br s, 1H), 6.90 (d, J=7.3 Hz, 1H), 5.42-5.54 (br s, 1H), 2.47 (s, 3H); ES-MS m/z 438.2 (MH)$^+$; HPLC RT (Method A) 2.57 min.

Intermediate V

Preparation of 4-amino-5-(3-chloro-4-nitrophenyl)pyrrolo[2,1-f][1,2,4]triazine-6-carboxylic acid

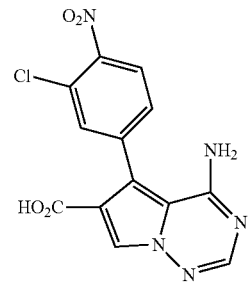

The procedure used for the preparation of Intermedate I was used to prepare the title compound by substituting Intermediate R for Intermediate H. $^1$H-NMR (300 MHz, DMSO-d$_6$) δ 12.47-12.56 (br s, 1H), 8.15 (s, 1H), 8.07 (d, J=8.2 Hz, 1H), 7.96 (s, 1H), 7.77 (d, J=1.8 Hz, 1H), 7.55 (dd, J=8.3, 1.8 Hz, 1H); ES-MS m/z 334.1 (MH)$^+$; HPLC RT (Method B) 2.45 min.

Intermediate W

Preparation of 4-amino-5-(3-chloro-4-nitrophenyl)-N-(2,2,2-trifluoroethyl)pyrrolo[2,1-f][1,2,4]triazine-6-carboxamide

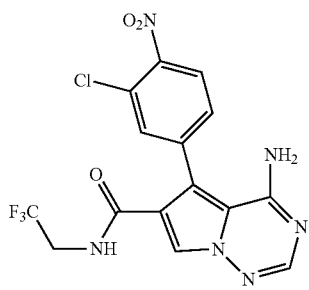

The procedure used for the preparation of Intermedate K was used to prepare the title compound by substituting Intermediate V for Intermediate J. $^1$H-NMR (300 MHz, DMSO-d$_6$) δ 8.79 (t, J=6.3 Hz, 1H), 8.28 (s, 1H), 8.06 (d, J=8.3 Hz, 1H), 7.97 (s, 1H), 7.68 (d, J=1.8 Hz, 1H), 7.48 (dd, J=8.2, 1.9 Hz, 1H) 3.91-4.01 (m, 2H); ES-MS m/z 415.1 (MH)$^+$; HPLC RT (Method A) 2.83 min.

Intermediate X

Preparation of 4-amino-5-(4-amino-3-chlorophenyl)-N-(2,2,2-trifluoroethyl)pyrrolo[2,1-f][1,2,4]triazine-6-carboxamide

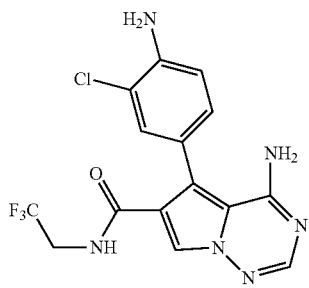

The procedure used for the preparation of Intermedate S was used to prepare the title compound by substituting Intermediate W for Intermediate R. $^1$H-NMR (300 MHz, DMSO-d$_6$) δ 8.44 (t, J=6.3 Hz, 1H), 8.13 (s, 1H), 7.91-8.02 (br s, 1H), 7.89 (s, 1H), 7.17 (d, J=2.0 Hz, 1H), 6.99 (dd, J=8.2, 2.0 Hz, 1H) 6.80 (d, J=8.5 Hz, 1H), 5.54 (s, 2H), 5.08-5.24 (br s, 1H), 3.88-4.00 (m, 2H); ES-MS m/z 385.1 (MH)$^+$; HPLC RT (Method A) 2.27 min.

Intermediate Y

Preparation of phenyl (6-methylpyridin-2-yl)carbamate

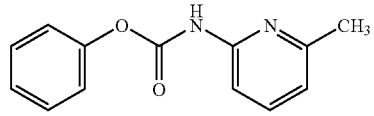

Phenyl chloroformate (232 mL, 1.84 mol) was added dropwise (1.5 h) to a cooled (0° C.) solution of 2-amino-6-picoline (200 g, 1.84 mol) and pyridine (448 mL, 5.55 mol) in THF (1.6 L). The reaction was stirred, with continued cooling for 15 h. Water (500 mL) was added slowly (30 min) and then the mixture was diluted with ethyl acetate (2 L). The layers were separated and the organic layer was washed with 1 N hydrochloric acid (3×1 L), 1 N aqueous sodium hydroxide solution (500 mL) and brine (500 mL). The organic layer was then dried over sodium sulfate and concentrated under reduced pressure. The residue was suspended in hexane (500 mL) for 30 min and then filtered to afford the desired product (220 g, 52%) containing some trace impurities. $^1$H-NMR (300 MHz, DMSO-d$_6$) δ 10.68 (s, 1H), 6.93-7.74 (m, 8H), 2.42 (s, 3H); ES-MS m/z 229.4 (MH)$^+$; HPLC RT (Method A) 2.94 min.

Intermediate Z

Preparation of phenyl (6-ethylpyridin-2-yl)carbamate

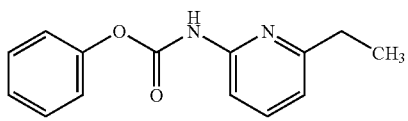

The procedure used for the formation of Intermediate Y was used to prepare the title compound by substituting 2-amino-6-ethylpyridine for 2-amino-6-picoline. $^1$H-NMR (300 MHz, DMSO-d$_6$) δ 10.60 (s, 1H), 6.67-7.73 (m, 8H), 2.64 (q, J=7.5 Hz, 2H) 1.24 (t, J=7.5 Hz, 3H); ES-MS m/z 243.1 (MH)+; HPLC RT (Method A) 2.46 min.

EXAMPLES

Example 1

Preparation of 4-amino-5-(3-fluoro-4-{[(6-methylpyridin-2-yl)carbamoyl]amino}phenyl)-N-methylpyrrolo[2,1-9 [1,2,4]triazine-6-carboxamide

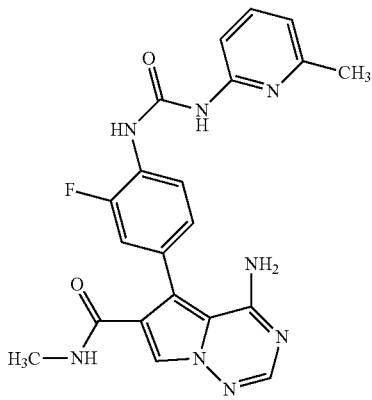

Intermediate I (75 mg, 0.18 mmol) was added to a mixture methylamine hydrochloride (60 mg, 0.89 mmol), benzotriazolyloxytris(dimethylamino)phosphonium PF6 (118 mg, 0.27 mmol) and 4-methylmorpholine (90 mg, 0.89 mmol) in DMF (2 mL). The reaction was stirred at it for 16 h and then filtered. The filtrate was subjected to HPLC purification using a gradient elution from 25% to 85% acetonitrile in water to give the desired product (25 mg, 32%); $^1$H NMR (300 MHz, DMSO-d$_6$) δ 9.93 (s, 1H), 8.32 (dd, J=8.4, 8.4 Hz, 1H), 8.07 (s, 1H), 7.90 (s, 1H), 7.88-7.97 (br s, 1H), 7.66 (dd, J=7.8, 7.8 Hz, 1H), 7.30 (dd, J=11.9, 1.9 Hz, 1H), 7.12 (dd, J=8.4, 1.8 Hz, 1H), 6.93-7.03 (br d, 1H), 6.90 (d J=7.4 Hz, 1H), 2.63 (d, J=4.6 Hz, 3H), 2.46 (s, 3H); ES-MS m/z 435.1 (MH)+; HPLC RT (Method A) 1.80 min.

Example 2

Preparation of 4-amino-N-ethyl-5-(3-fluoro-4-{[(6-methylpyridin-2-yl)carbamoyl]amino}phenyl)pyrrolo[2,1-f][1,2,4]triazine-6-carboxamide

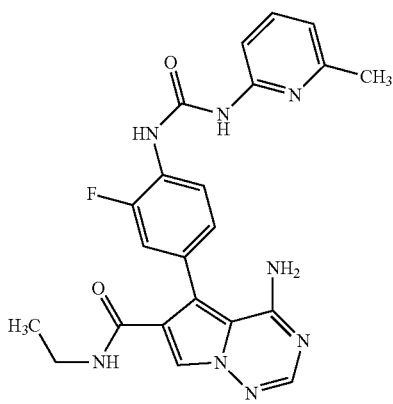

The procedure used for the preparation of Example 1 was used to prepare the title compound by substituting ethylamine hydrochloride for methylamine hydrochloride. $^1$H NMR (300 MHz, DMSO-d$_6$) δ 9.93 (s, 1H), 8.32 (dd, J=8.4, 8.4 Hz, 1H), 8.09 (s, 1H), 7.90 (s, 1H), 7.84-7.95 (br s, 1H), 7.66 (dd, J=7.7, 7.7 Hz, 1H), 7.30 (dd, J=12.0, 1.8 Hz, 1H), 7.12 (dd, J=8.4, 1.7 Hz, 1H), 6.96-7.05 (br d, 1H), 6.90 (d J=7.4 Hz, 1H), 3.06-3.19 (m, 2H), 2.46 (s, 3H), 1.08 (t, J=7.2 Hz, 3H); ES-MS m/z 449.1 (MH)+; HPLC RT (Method B) 2.44 min.

Example 3

Prepration of 4-amino-5-(3-fluoro-4-{[(6-methylpyridin-2-yl)carbamoyl]amino}phenyl)-N-propylpyrrolo[2,1-f][1,2,4]triazine-6-carboxamide

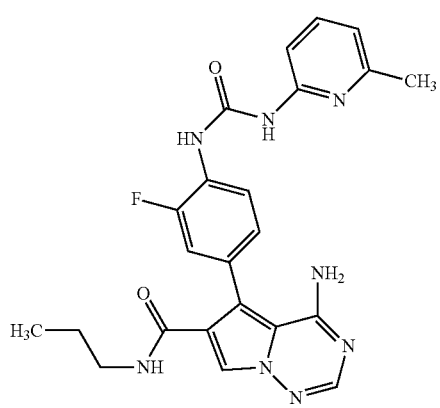

The procedure used for the preparation of Example 1 was used to prepare the title compound by substituting propylamine for methylamine hydrochloride. $^1$H NMR (300 MHz, DMSO-d$_6$) δ 9.93 (s, 1H), 8.32 (dd, J=8.5, 8.5 Hz, 1H), 8.09 (s, 1H), 7.90 (s, 1H), 7.86 (dd, J=5.7, 5.7 Hz, 1H), 7.66 (dd, J=7.8, 7.8 Hz, 1H), 7.30 (dd, J=12.2, 2.0 Hz, 1H), 7.12 (dd, J=8.3, 1.7 Hz, 1H), 6.95-7.04 (br d, 1H), 6.90 (d J=7.4 Hz, 1H), 3.05 (q, J=6.5 Hz, 2H), 2.45 (s, 3H), 1.33-1.44 (m, 2H), 0.79 (t, J=7.4 Hz, 3H); ES-MS m/z 463.1 (MH)+; HPLC RT (Method B) 2.59 min.

Example 4

Preparation of 4-amino-5-(3-fluoro-4-{[(6-methylpyridin-2-yl)carbamoyl]amino}phenyl)-N-(2,2,2-trifluoroethyl)pyrrolo[2,1-f][1,2,4]triazine-6-carboxamide

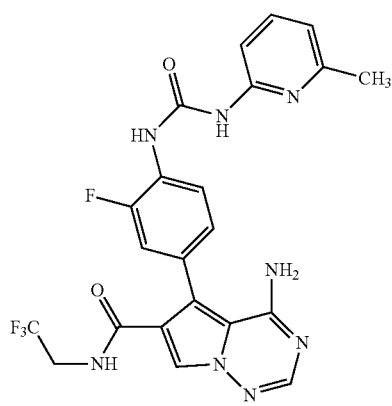

The procedure used for the preparation of Example 1 was used to prepare the title compound by substituting 2,2,2-trifluouro-1-aminoethane for methylamine hydrochloride. $^1$H NMR (300 MHz, DMSO-$d_6$) δ 9.94 (s, 1H), 8.58 (dd, J=6.4, 6.4 Hz, 1H), 8.33 (dd, J=8.4, 8.4 Hz, 1H), 8.20 (s, 1H), 7.93 (s, 1H), 7.66 (dd, J=7.9, 7.9 Hz, 1H), 7.30 (dd, J=12.2, 1.9 Hz, 1H), 7.12 (dd, J=8.4, 1.8 Hz, 1H), 6.96-7.04 (br d, 1H), 6.91 (d J=7.5 Hz, 1H), 3.90-4.01 (m, 2H), 2.46 (s, 3H); ES-MS m/z 503.2 (MH)$^+$; HPLC RT (Method A) 3.00 min.

Example 5

Preparation of 4-amino-5-(3-fluoro-4-{[(6-methylpyridin-2-yl)carbamoyl]amino}phenyl)-N-isobutylpyrrolo[2,1-f][1,2,4]triazine-6-carboxamide

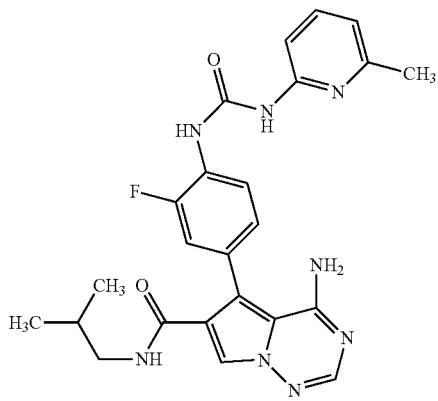

The procedure used for the preparation of Example 1 was used to prepare the title compound by substituting iso-butylamine for methylamine hydrochloride. $^1$H NMR (300 MHz, DMSO-$d_6$) δ 9.93 (s, 1H), 8.33 (dd, J=8.5, 8.5 Hz, 1H), 8.09 (s, 1H), 7.91 (s, 1H), 7.81 (dd, J=5.7, 5.7 Hz, 1H), 7.66 (dd, J=7.8, 7.8 Hz, 1H), 7.30 (dd, J=12.1, 1.9 Hz, 1H), 7.13 (dd, J=8.2, 1.6 Hz, 1H), 6.96-7.04 (br d, 1H), 6.90 (d, J=7.4 Hz, 1H), 2.92 (t, J=6.4 Hz, 2H), 2.45 (s, 3H), 1.61-1.72 (m, 2H), 0.78 (d, J=7.6 Hz, 3H); ES-MS m/z 477.1 (MH)$^+$; HPLC RT (Method A) 3.02 min.

Example 6

Preparation of 4-amino-N-cyclopropyl-5-(3-fluoro-4-{[(6-methylpyridin-2-yl)carbamoyl]amino}phenyl)pyrrolo[2,1-f][1,2,4]triazine-6-carboxamide

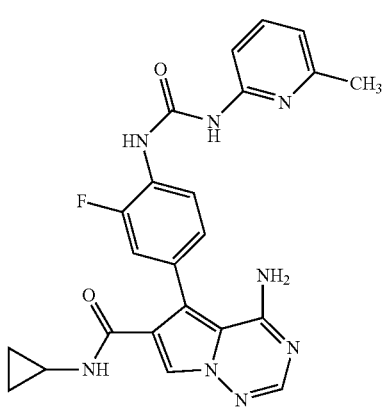

The procedure used for the preparation of Example 1 was used to prepare the title compound by substituting cyclopropylamine for methylamine hydrochloride. $^1$H NMR (300 MHz, DMSO-$d_6$) δ 9.95 (s, 1H), 8.34 (dd, J=8.3, 8.3 Hz, 1H), 8.09 (s, 1H), 7.98 (d, J=4.1 Hz, 1H), 7.92 (s, 1H), 7.68 (dd, J=7.9, 7.9 Hz, 1H), 7.31 (dd, J=12.2, 1.8 Hz, 1H), 7.13 (dd, J=8.4, 1.7 Hz, 1H), 6.98-7.08 (br d, 1H), 6.92 (d J=7.4 Hz, 1H), 2.62-2.71 (m, 2H), 2.48 (s, 3H), 0.58-0.65 (m, 2H), 0.40-0.47 (m, 2H); ES-MS m/z 461.2 (MH)$^+$; HPLC RT (Method A) 2.56 min.

Example 7

Preparation of 4-amino-N-ethyl-5-(3-fluoro-4-{[(6-methylpyridin-2-yl)carbamoyl]amino}phenyl)-N-methylpyrrolo[2,1-f][1,2,4]triazine-6-carboxamide

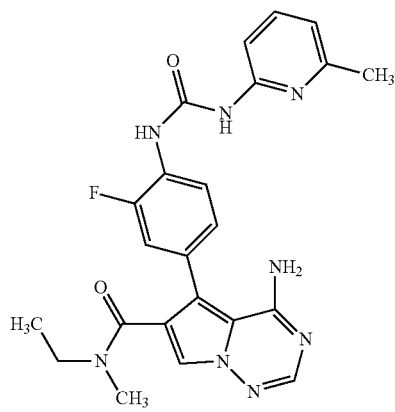

The procedure used for the preparation of Example 1 was used to prepare the title compound by substituting N-ethyl-N-methylamine for methylamine hydrochloride. $^1$H NMR (300 MHz, DMSO-$d_6$) δ 9.93 (s, 1H), 8.36 (dd, J=8.5, 8.5 Hz, 1H), 7.91 (s, 1H), 7.87 (s, 1H), 7.66 (dd, J=7.4, 7.4 Hz, 1H), 7.28-7.37 (m, 1H), 7.10-7.15 (m, 1H), 6.95-7.03 (br d, 1H), 6.90 (d J=7.4 Hz, 1H), 3.05-3.37 (m, 2H), 2.81 and 2.60 (2s, 3H), 2.44 (s, 3H), 0.78-0.96 (m, 3H); ES-MS m/z 463.1 (MH)$^+$; HPLC RT (Method A) 2.90 min.

Example 8

Preparation of 4-amino-N-[2-(dimethylamino)ethyl]-5-(3-fluoro-4-{[(6-methylpyridin-2-yl)carbamoyl]amino}phenyl)pyrolo[2,1-f][1,2,4]triazine-6-carboxamide

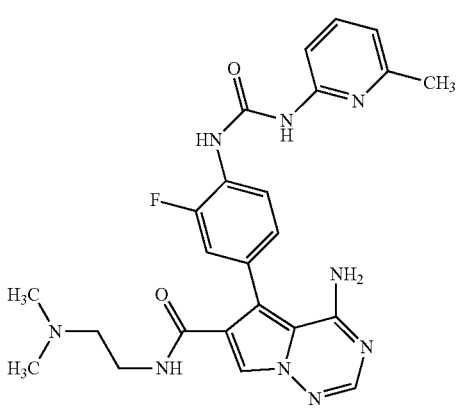

The procedure used for the preparation of Example 1 was used to prepare the title compound by substituting N,N-dimethylethylenediamine for methylamine hydrochloride. $^1$H NMR (300 MHz, DMSO-$d_6$) δ 9.94 (s, 1H), 8.37 (dd, J=8.4, 8.4 Hz, 1H), 8.06 (s, 1H), 7.90 (s, 1H), 7.66 (dd, J=7.7, 7.7 Hz, 1H), 7.30-7.40 (m, 1H), 7.13-7.19 (m, 1H), 6.96-7.03 (br d, 1H), 6.90 (d J=7.4 Hz, 1H), 3.17 (q, J=6.6 Hz, 2H), 2.45 (s, 3H), 2.21 (t, J=6.6 Hz, 2H), 2.03 (s, 6H); MS [M+H]$^+$=492.1; LCMS RT=1.97 min (Method B). ES-MS m/z 492.1 (MH)$^+$; HPLC RT (Method B) 1.97 min.

Example 9

Preparation of 4-amino-N-tert-butyl-5-(3-fluoro-4-{[(6-methylpyridin-2-yl)carbamoyl]amino}phenyl)pyrrolo[2,1-f][1,2,4]triazine-6-carboxamide

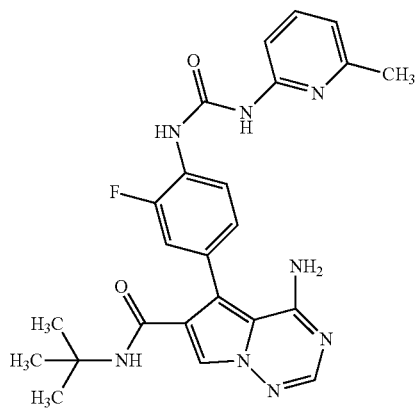

The procedure used for the preparation of Example 1 was used to prepare the title compound by substituting tert-butylamine for methylamine hydrochloride. $^1$H NMR (300 MHz, DMSO-$d_6$) δ 9.94 (s, 1H), 8.37 (dd, J=8.4, 8.4 Hz, 1H), 8.05 (s, 1H), 7.89 (s, 1H), 7.66 (dd, J=8.0, 8.0 Hz, 1H), 7.33 (dd, J=12.0, 1.9 Hz, 1H), 7.13 (dd, J=8.5, 1.7 Hz, 1H), 6.97-7.04 (br d, 1H), 6.93 (s, 1H), 6.90 (d J=7.4 Hz, 1H), 2.45 (s, 3H), 1.20 (s, 9H); ES-MS m/z 477.2 (MH)$^+$; HPLC RT (Method A) 2.67 min.

Example 10

Preparation of 4-amino-N-tert-butyl-5-(4-{[(6-ethylpyridin-2-yl)carbamoyl]amino}-3-fluorophenyl)pyrrolo[2,1-f][1,2,4]triazine-6-carboxamide

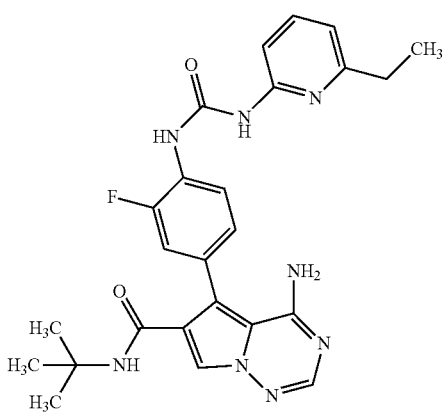

The procedure used for the preparation of Intermediate H was used to prepare the title compound by substituting Intermediate L for Intermediate G and phenyl (6-ethylpyridin-2-yl)carbamate for of phenyl (6-methylpyridin-2-yl)carbamate. $^1$H NMR (300 MHz, DMSO-$d_6$) δ 9.93 (s, 1H), 8.35 (dd, J=8.4, 8.4 Hz, 1H), 8.05 (s, 1H), 7.89 (s, 1H), 7.68 (dd, J=8.2, 7.5 Hz, 1H), 7.32 (dd, J=11.8, 2.0 Hz, 1H), 7.15 (dd, J=8.5, 1.8 Hz, 1H), 6.98-7.06 (br d, 1H), 6.89-6.95 (m, 2H), 2.73 (q, J=7.4 Hz, 2H), 1.26 (t, J=7.4 Hz, 3H), 1.21 (s, 9H); ES-MS m/z 491.3 (MH)$^+$; HPLC RT (Method A) 3.10 min.

Example 11

Preparation of 4-amino-5-(4-{[(6-ethylpyridin-2-yl)carbamoyl]amino}-3-fluorophenyl)-N-(2,2,2-trifluoroethyl)pyrrolo[2,1-f][1,2,4]triazine-6-carboxamide

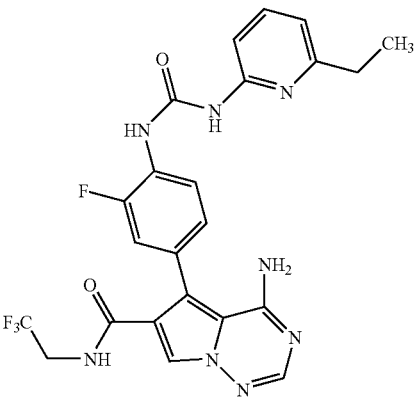

The procedure used for the preparation of Intermediate H was used to prepare the title compound by substituting Intermediate K for Intermediate G and phenyl (6-ethylpyridin-2-yl)carbamate for of phenyl (6-methylpyridin-2-yl)carbamate. $^1$H NMR (300 MHz, DMSO-$d_6$) δ 9.93 (s, 1H), 8.58 (dd, J=6.4, 6.4 Hz, 1H), 8.32 (dd, J=8.4, 8.4 Hz, 1H), 8.20 (s, 1H), 7.93 (s, 1H), 7.68 (dd, J=7.8, 7.8 Hz, 1H), 7.29 (dd, J=12.0, 1.9 Hz, 1H), 7.12 (dd, J=8.5, 2.0 Hz, 1H), 6.98-7.05 (br d, 1H), 6.91 (d J=7.5 Hz, 1H), 3.89-4.00 (m, 2H), 2.72 (q, J=7.6 Hz, 2H), 1.25 (t, J=7.6 Hz, 3H); ES-MS m/z 517.2 (MH)$^+$; HPLC RT (Method B) 2.89 min.

Example 12

Preparation of 4-amino-5-(3-chloro-4-{[(6-methylpyridin-2-yl)carbamoyl]amino}phenyl)-N-ethylpyrro[2,1-f][1,2,4]triazine-6-carboxamide

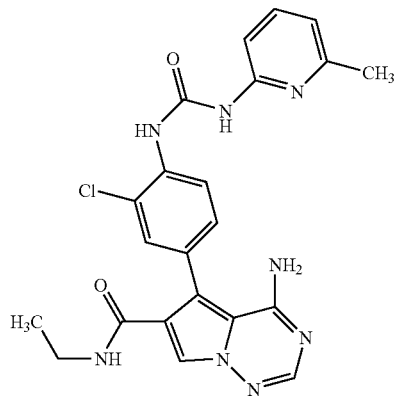

The procedure used for the preparation of Example 1 was used to prepare the title compound by substituting Intermediate U for Intermediate I and ethylamine hydrochloride for methylamine hydrochloride. $^1$H-NMR (300 MHz, DMSO-$d_6$) δ 10.01 (s, 1H), 8.38 (d, J=8.6 Hz, 1H), 8.10 (s, 1H), 7.95 (dd, J=5.5, 5.5 Hz, 1H), 7.91 (s, 1H), 7.62-7.70 (m, 1H), 7.49 (d, J=2.1 Hz, 1H), 7.28 (dd, J=8.6, 2.0 Hz, 1H), 6.91-7.00 (br s, 1H), 6.90 (d, J=7.4 Hz, 1H), 5.27-5.38 (br s, 1H), 3.07-3.17 (m, 2H), 2.47 (s, 3H), 1.11 (t, J=7.2 Hz, 3H); ES-MS m/z 465.2 (MH)$^+$; HPLC RT (Method A) 2.90 min.

Example 13

Preparation of 4-amino-5-(3-chloro-4-{[(6-methylpyridin-2-yl)carbamoyl]amino}phenyl)-N-propylpyrrolo[2,1-f][1,2,4]triazine-6-carboxamide

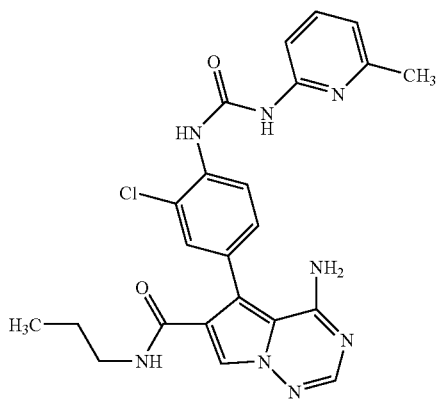

The procedure used for the preparation of Example 1 was used to prepare the title compound by substituting Intermediate U for Intermediate I and n-propylamine for methylamine hydrochloride. $^1$H-NMR (300 MHz, DMSO-$d_6$) δ 10.01 (s, 1H), 8.38 (d, J=8.5 Hz, 1H), 8.10 (s, 1H), 7.89-7.96 (m, 2H), 7.62-7.70 (m, 1H), 7.49 (d, J=1.8 Hz, 1H), 7.28 (dd, J=8.5, 2.0 Hz, 1H), 6.91-6.99 (br s, 1H), 6.90 (d, J=7.4 Hz, 1H), 5.24-5.37 (br s, 1H), 3.06 (q, J=6.5 Hz, 2H), 2.47 (s, 3H), 1.35-1.46 (m, 2H), 0.80 (t, J=7.4 Hz, 3H); ES-MS m/z 479.2 (MH)$^+$; HPLC RT (Method B) 2.79 min.

Example 14

Preparation of 4-amino-5-(3-chloro-4-{[(6-methylpyridin-2-yl)carbamoyl]amino}phenyl)-N-cyclopropylpyrrolo[2,1-f][1,2,4]triazine-6-carboxamide

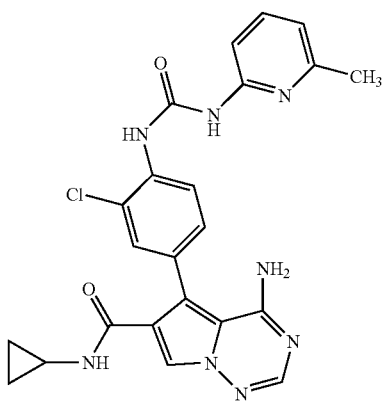

The procedure used for the preparation of Example 1 was used to prepare the title compound by substituting Intermediate U for Intermediate I and cyclopropylamine for methylamine hydrochloride. $^1$H-NMR (300 MHz, DMSO-$d_6$) δ 10.02 (s, 1H), 8.38 (d, J=8.5 Hz, 1H), 8.08 (s, 1H), 8.01 (d, J=3.8 Hz, 1H), 7.90 (s, 1H), 7.62-7.70 (m, 1H), 7.49 (d, J=2.1 Hz, 1H), 7.29 (dd, J=8.5, 2.1 Hz, 1H), 6.91-7.01 (br s, 1H), 6.90 (d, J=7.5 Hz, 1H), 5.21-5.39 (br s, 1H), 2.62-2.69 (m, 1H), 2.47 (s, 3H), 0.56-0.63 (m, 2H), 0.38-0.45 (m, 2H); ES-MS m/z 477.2 (MH)$^+$; HPLC RT (Method B) 2.89 min.

Example 15

Preparation of 4-amino-5-(3-chloro-4-{[(6-methylpyridin-2-yl)carbamoyl]amino}phenyl)-N-[2-(dimethylamino)ethyl]pyrrolo[2,1-f][1,2,4]triazine-6-carboxamide

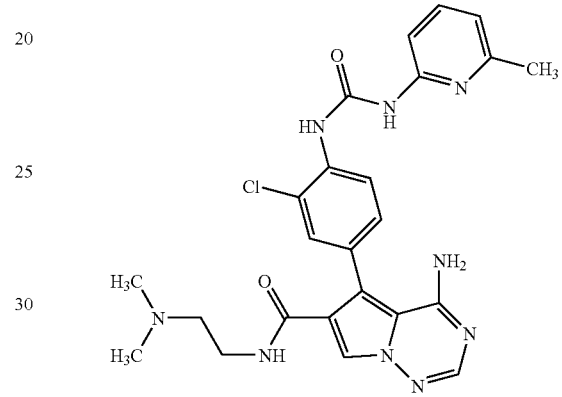

The procedure used for the preparation of Example 1 was used to prepare the title compound by substituting Intermediate U for Intermediate I and N,N-dimethylethylenediamine for methylamine hydrochloride. $^1$H-NMR (300 MHz, DMSO-$d_6$) δ 10.03 (s, 1H), 8.42 (d, J=8.5 Hz, 1H), 8.07 (s, 1H), 7.91 (s, 1H), 7.62-7.70 (m, 1H), 7.51 (d, J=2.0 Hz, 1H), 7.45-7.51 (br s, 1H), 7.31 (dd, J=8.5, 1.9 Hz, 1H), 6.91-7.00 (br s, 1H), 6.90 (d, J=7.4 Hz, 1H), 5.21-5.34 (br s, 1H), 3.18 (q, J=6.1 Hz, 2H), 2.47 (s, 3H), 2.20-2.27 (m, 2H), 2.06 (s, 6H); ES-MS m/z 508.1 (MH)$^+$; HPLC RT (Method B) 2.17 min.

Example 16

Preparation of 4-amino-5-(3-chloro-4-{[(6-methylpyridin-2-yl)carbamoyl]amino}phenyl)-N-(2,2,2-trifluoroethyl)pyrrolo[2,1-f][1,2,4]triazine-6-carboxamide

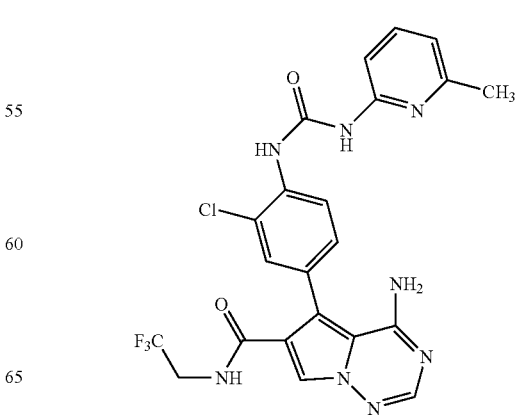

The procedure used for the preparation of Intermediate H was used to prepare the title compound by substituting Intermediate X for Intermediate G. ¹H-NMR (300 MHz, DMSO-d₆) δ 10.01 (s, 1H), 8.63 (t, J=6.4 Hz, 1H), 8.39 (d, J=8.4 Hz, 1H), 8.21 (s, 1H), 7.93 (s, 1H), 7.62-7.70 (m, 1H), 7.48 (d, J=1.8 Hz, 1H), 7.28 (dd, J=8.6, 2.0 Hz, 1H), 6.91-6.99 (br s, 1H), 6.90 (d, J=7.3 Hz, 1H), 5.31-5.42 (br s, 1H), 3.91-4.01 (m, 2H), 2.47 (s, 3H); ES-MS m/z 519.2 (MH)⁺; HPLC RT (Method B) 2.87 min.

Example 17

Preparation of 4-amino-5-(3-chloro-4-{1(6-ethylpyridin-2-yl)carbamoyl]amino}phenyl)-N-(2,2,2-trifluoroethyl)pyrrolo[2,1-f][1,2,4]triazine-6-carboxamide

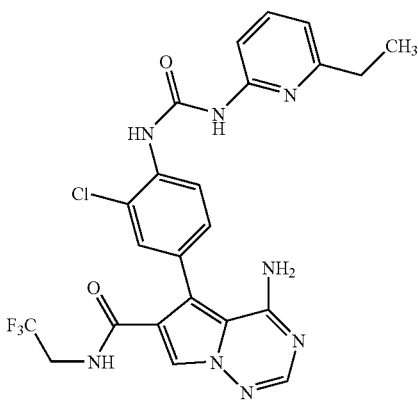

The procedure used for the preparation of Intermediate H was used to prepare the title compound by substituting Intermediate X for Intermediate G and phenyl (6-ethylpyridin-2-yl)carbamate for of phenyl (6-methylpyridin-2-yl)carbamate. ¹H-NMR (300 MHz, DMSO-d₆) δ 10.02 (s, 1H), 8.63 (t, J=6.3 Hz, 1H), 8.36 (d, J=8.7 Hz, 1H), 8.21 (s, 1H), 7.93 (s, 1H), 7.65-7.72 (m, 1H), 7.48 (d, J=2.0 Hz, 1H), 7.28 (dd, J=8.5, 2.0 Hz, 1H), 6.97-7.06 (br s, 1H), 6.91 (d, J=7.4 Hz, 1H), 5.29-5.39 (br s, 1H), 3.90-4.01 (m, 2H), 2.75 (q, J=7.6 Hz, 2H), 1.23 (t, J=7.6 Hz, 3H); MS [M+H]⁺=533.2; LCMS RT=3.02 min (Method B). ES-MS m/z 533.2 (MH)⁺; HPLC RT (Method B) 3.02 min.

Example 18

Preparation of 4-amino-5-(3-fluoro-4-{[(6-methylpyridin-2-yl)carbamoyl]amino}phenyl)-N-(2,2,2-trifluoroethyl)pyrrolo[2,1-f][1,2,4]triazine-6-carboxamide dimethanesulfonate

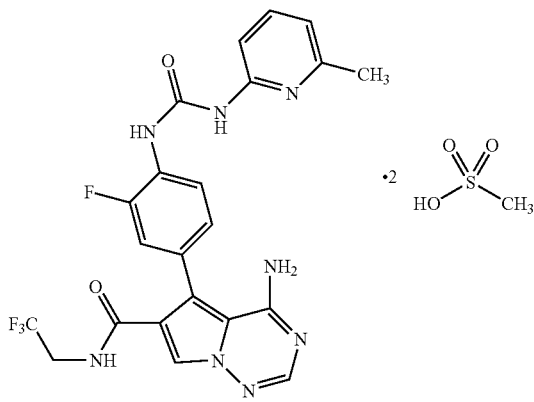

To 4-amino-5-(3-fluoro-4-{[(6-methylpyridin-2-yl)carbamoyl]amino}phenyl)-N-(2,2,2-trifluoroethyl)pyrrolo[2,1-f][1,2,4]triazine-6-carboxamide (5.9 g) was added THF (650 mL). The mixture was heated until dissolution took place (up to 80° C.). In a separate flask methane sulfonic acid (2.5 mL) was diluted with THF (25 mL). 17 mL of the methane sulfonic acid solution in THF was added to the solution of 4-amino-5-(4-{[(6-methylpyridin-2-yl)carbamoyllamino}phenyl)-N-(2,2,2-trifluoroethyl)pyrrolo[2,1-f][1,2,4]triazine-6-carboxamide in THF. The mixture was left to stir for 16 h. The solid was filtered using a 0.2 uM membrane filter. The solid was dried to give 7.91 g (97%) of the title compound. ¹H NMR (300 MHz, DMSO-d₆) δ 9.95 (s, 1H), 8.68 (t, 1H), 8.60 (br s, 1H), 8.38 (t, 1H), 8.30 (s, 1H), 8.03 (s, 1H), 7.70 (t, 1H), 7.30 (d, 1H), 7.18 (d, 1H), 7.02 (bd, 1H), 6.85 (d, 1H), 3.98 (m, 2H), 2.54 (s, 3H), 2.32 (s, 6H); ES-MS m/z 503.30 (MH)⁺, HPLC RT (Method A) 2.64 min. DSC mp.=249.97° C. (after stirring in MeOH for 1 Week and drying mp.=258.99° C.) Anal. Calc'd for $C_{22}H_{18}F_4N_8O_2 \cdot 2(CH_4O_3S)$: C, 41.50%; H, 3.77%; F, 10.94%; N, 16.13%; O, 18.43%; S, 9.23%. Found: C, 41.21%; H, 3.51%; N, 15.69%. Karl Fischer Titration: 0.96% water.

Example 19

Preparation of 4-amino-5-(3-fluoro-4-{[(6-methylpyridin-2-yl)carbamoyl]amino}phenyl)-N-(2,2,2-trifluoroethyl)pyrrolo[2,1-f][1,2,4]triazine-6-carboxamide hydrochloride

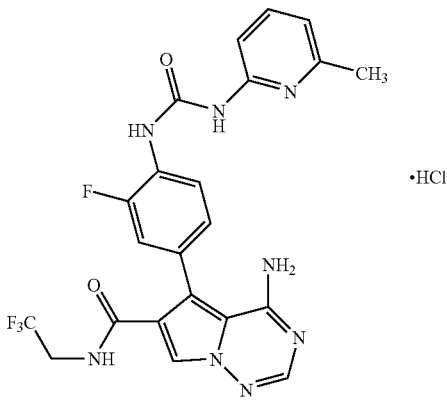

The procedure used for the prepartation of Example 18 was used prepare the title compound by substituting hydrochloric acid for methane sulfonic acid. ¹H NMR (300 MHz, DMSO-d₆) δ 10.03 (s, 1H), 9.08 (br s, 1H), 8.75 (t, 1H), 8.47 (m, 2H), 8.17 (s, 1H), 7.68 (t, 1H), 7.34 (d, 1H), 7.15 (d, 1H), 7.05 (bd, 1H), 6.93 (d, 1H), 3.98 (m, 2H), 2.54 (s, 3H); ES-MS m/z 503.10 (MH)⁺, HPLC RT (Method A) 2.80 min. DSC mp.=248.84° C. (mp=251.43° C. after stirring in methanol for one week and dried) Anal. Calcd for $C_{22}H_{18}F_4N_8O_2 \cdot HCl$: C, 49.03%; H, 3.55%; N, 20.79%. Found: C, 48.89%; H, 3.55%; N, 20.46%.

Example 20

Preparation of 4-amino-5-(3-fluoro-4-{[(6-methylpyridin-2-yl)carbamoyl]amino}phenyl)-N-(2,2,2-trifluoroethyl)pyrrolo[2,1-f][1,2,4]triazine-6-carboxamide dif(2Z)-but-2-enedioate]

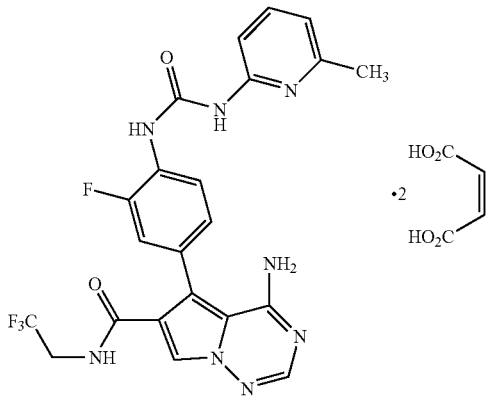

To a solution of 4-amino-5-(3-fluoro-4-{[(6-methylpyridin-2-yl)carbamoyl]amino}phenyl)-N-(2,2,2-trifluoroethyl)pyrrolo[2,1-f][1,2,4]triazine-6-carboxamide (3.7 g, 7.36 mmol) in THF (480 mL) was added a solution of maleic acid (22 mL, 22 mol, 2.9 g was dissolved in 25 mL of THF to make a 1 M solution) and the mixture was stirred at rt for 16 h. The solid was filtered using a 0.2 uM membrane filter, dried in high vacuum oven to give (4.87 g, 90%) of the title compound. $^1$H NMR (300 MHz, DMSO-$d_6$) δ 9.95 (s, 1H), 8.60 (t, 1H), 8.36 (t, 1H), 8.21 (s, 1H), 7.94 (s, 1H), 7.66 (t, 1H), 7.30 (d, 1H), 7.11 (d, 1H), 6.96 (bd, 1H), 6.89 (d, 1H), 6.95 (s, 4H), 3.98 (m, 2H), 2.50 (s, 3H); ES-MS m/z 503.30 (MH)$^+$, HPLC RT (Method A) 2.64 min. DSC mp.=201.29° C. Anal. Calcd for $C_{22}H^{18}F_4N_8O_2 \cdot 2(C_4H_4O_4)$: C, 49.05%; H, 3.57%; N, 15.25%. Found: C, 49.19%; H, 3.63%; N 15.06%.

Example 21

Preparation of 4-amino-5-(3-fluoro-4-{[(6-methylpyridin-2-yl)carbamoyl]amino}phenyl)-N-(2,2,2-trifluoroethyl)pyrrolo[2,1-f][1,2,4]triazine-6-carboxamide (2E)-but-2-enedioate (2:1)

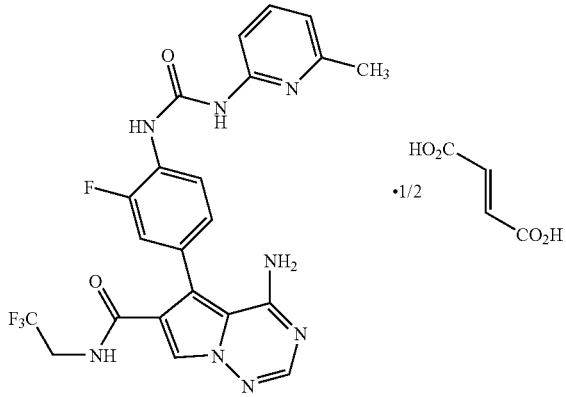

A solution of 4-amino-5-(3-fluoro-4-{[(6-methylpyridin-2-yl)carbamoyl]amino}phenyl)-N-(2,2,2-trifluoroethyl)pyrrolo[2,1-f][1,2,4]triazine-6-carboxamide (8.0 g) in THF (800 mL) was heated until dissolution took place (up to 80° C.). The reaction mixture was cooled to it and fumaric acid (1.38 g, 11.9 mmol) was added. The mixture was left to stir for 16 h. The solid was filtered using a 0.2 uM membrane filter. The solid was dried to give 6.35 g (71%) of the title compound. $^1$H NMR (300 MHz, DMSO-$d_6$) δ 9.95 (s, 1H), 8.68 (t, 1H), 8.35 (t, 1H), 8.23 (s, 1H), 7.95 (s, 1H), 7.65 (t, 1H), 7.32 (d, 1H), 7.17 (d, 1H), 7.05 (bd, 1H), 6.95 (d, 1H), 6.61 (s, 1H), 3.98 (m, 2H), 2.54 (s, 3H); ES-MS m/z 503.30 (MH)$^+$, HPLC RT (Method A) 2.63 min. DSC mp.=229.54° C. Anal. Calc'd for $C_{22}H_{18}F_4N_8O_2 \cdot 0.5(C_4H_4O_4)$: C, 51.43%; H, 3.60%; F, 13.56%; N, 19.99%; O, 11.42%; Found: C, 50.90%; H, 3.78%; N, 19.67%.

Example 22

Preparation of 4-amino-5-(3-fluoro-4-{[(6-methylpyridin-2-yl)carbamoyl]amino}phenyl)-N-(2,2,2-trifluoroethyl)pyrrolo[2,1-f][1,2,4]triazine-6-carboxamide hydrobromide

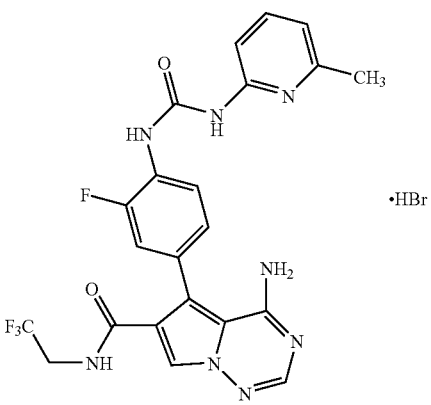

The procedure used for the prepartation of Example 18 was used prepare the title compound by substituting hydrobromic acid (30% in acetic acid) for methane sulfonic acid. $^1$H NMR (300 MHz, DMSO-$d_6$) δ 9.95 (s, 1H), 8.68 (t, 1H), 8.60 (br s, 1H), 8.38 (t, 1H), 8.30 (s, 1H), 8.03 (s, 1H), 7.70 (t, 1H), 7.30 (d, 1H), 7.18 (d, 1H), 7.02 (bd, 1H), 6.85 (d, 1H), 3.98 (m, 2H), 2.54 (s, 3H); ES-MS m/z 503.26 (MH)$^+$, HPLC RT (Method A) 2.74 min. DSC mp.=249.18° C. Anal. Calcd for $C_{22}H_{18}F_4N_8O_2 \cdot HBr$: C, 45.30%; H, 3.28%; Br, 13.70%; F, 13.03%; N, 19.21%; O, 5.49%. Found: C, 45.30%; H, 3.28%; N, 19.21%.

Example 23

Preparation of 4-amino-5-(4-{[(6-methylpyridin-2-yl)carbamoyl]amino}phenyl)-N-(2,2,2-trifluoroethyl)pyrrolo[2,1-f][1,2,4]triazine-6-carboxamide oxalate

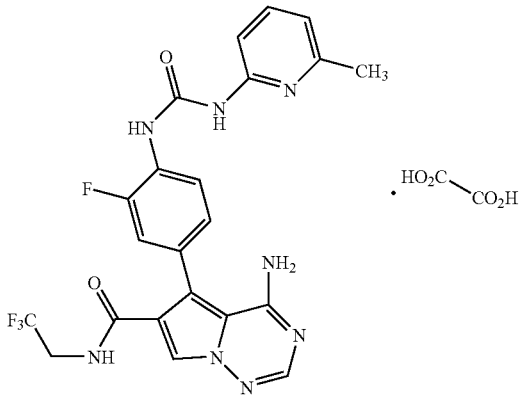

To a solution of 4-amino-5-(3-fluoro-4-{[(6-methylpyridin-2-yl)carbamoyl]amino}phenyl)-N-(2,2,2-trifluoroethyl)pyrrolo[2,1-f][1,2,4]triazine-6-carboxamide (100 mg, 0.2 mmol) in THF (5 mL) was added 1M solution of oxalic acid (0.2 mL, 0.2 mmol, 225 mg was dissolved in 2.5 mL of THF to make a 1M solution) and the mixture was stirred at rt for 16 h. The solid was filtered using a 0.2 uM membrane filter, dried in high vacuum oven to give (60 mg, 51%) of the title compound. $^1$H NMR (300 MHz, DMSO-$d_6$) δ 9.95 (s, 1H), 8.60 (t, 1H), 8.36 (t, 1H), 8.21 (s, 1H), 7.94 (s, 1H), 7.66 (t, 1H), 7.30 (d, 1H), 7.11 (d, 1H), 6.96 (bd, 1H), 6.89 (d, 1H), 3.98 (m, 2H), 2.50 (s, 3H); ES-MS m/z 503.30 (MH)$^+$, HPLC RT (Method A) 2.64 min. DSC mp.=210.36° C. Anal. Calcd for $C_{22}H_{18}F_4N_8O_2$: $C_2H_2O_4$: C, 48.66%; H, 3.40%; N, 18.91%. Found: C, 48.62%; H, 3.24%; N 18.69%.

In additional experiments the amount of oxalic acid was varied from 1 to 10 equivalents n all cases the mono-oxalate salt was isolated.

Example 24

Preparation of 4-amino-5-(4-{[(6-methylpyridin-2-yl)carbamoyl]amino}phenyl)-N-(2,2,2-trifluoroethyl)pyrrolo[2,1-f][1,2,4]triazine-6-carboxamide bis-benzenesulfonate

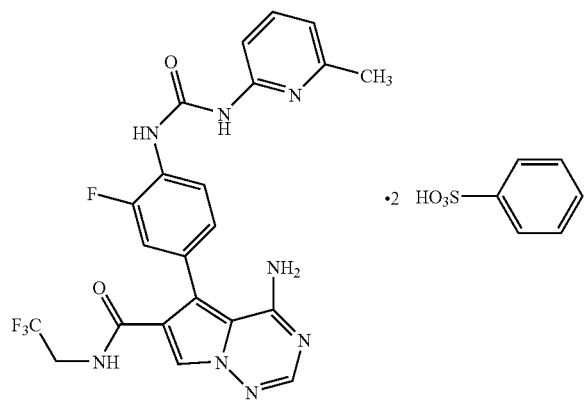

The procedure used for the prepartation of Example 18 was used prepare the title compound by substituting benzene sulfonic acid (1 equivalent) for methane sulfonic acid. Despite using only 1 equivalent the bis(benzene sulfonate) salt was isolated (45% yield). $^1$H NMR (300 MHz, DMSO-$d_6$) δ 9.95 (s, 1H), 8.68 (t, 1H), 8.60 (br s, 1H), 8.38 (t, 1H), 8.30 (s, 1H), 8.03 (s, 1H), 7.70 (t, 1H), 7.60 (m, 4H), 7.30 (m, 7H), 7.18 (d, 1H), 7.02 (bd, 1H), 6.92 (d, 1H), 3.98 (m, 2H), 2.54 (s, 3H); ES-MS m/z 503.32 (MH)$^+$, HPLC RT (Method A) 2.67 min. DSC mp.=232.60° C. Single Pulse 600 MHz NMR confirmed the ratio of free base to benzene sulfonate.

Physiological Activity

The utility of the compounds of the present invention can be illustrated, for example, by their activity in vitro in the Aurora 1 and 2 biochemical and Aurora 1 autophosphorylation assays described before. The link between Aurora Kinase inhibition and activity in human tumor xenograft models in mice has been established (Harrington et al. *Nature Medicine* 2004, 10 (3), 262). Furthermore, it has been very well established in the art that activity in human tumor xenograft models is associated with anti-tumor activity in the clinical setting. For example, the therapeutic utility of taxol (Silvestrini et al. *Stem Cells* 1993, 11(6), 528-35), taxotere (Bissery et al. *Anti Cancer Drugs* 1995, 6(3), 339), and topoisomerase inhibitors (Edelman et al. *Cancer Chemother. Pharmacol.* 1996, 37(5), 385-93) were demonstrated with the use of in vivo tumor xenograft models The in vitro effect of the compounds according to the invention can be demonstrated in the following assays:

Using a Scintillation Proximity Assay (SPA) format, the murine Aurora Kinase 1 (mAur1) and murine Aurora Kinase 2 (mAur2) biochemical assay measures the ability of mAur2 to phosphorylate the substrate, biotinylated Peptide 830 (DRT, Protein Sciences). Once radiolabeled by the enzyme, the biotinylated substrate is captured on streptavidin-coated SPA beads and the radioactivity, in proximity to the SPA beads, is measured. For the generation of $IC_{50}$ curves, the reaction was performed in 96-well isoplates (Wallac 1450-514) under the following conditions: a 10 mM stock solution of compound (in 100% dimethylsulfoxide; DMSO) was diluted 10 fold in 100% DMSO. Compounds were then serially diluted, 1:5, for an eight point dose curve, in 100% DMSO. A volume of 1 μL of the diluted compound was added to the reaction buffer that consisted of 25 mM HEPES pH 7.5, 1 mM $MnCl_2$, 1mM $MgCl_2$, 1 mM DTT, 0.01% Tween20. A mixture with a final concentration per well of 1 μM cold ATP, 0.1 μCi $^{33}$P-ATP (Amersham AH9968) and 1 μM biotinylated Peptide 830 was then added. The reaction was initiated with the addition of either recombinant, GST-tagged mAur 1 (amino acids 67-345) that was co-expressed with human INCENP(amino acids 704-919) (DRT, Protein Sciences) at a final concentration of 12 nM or N-terminal His-tagged mAur2 (amino acids 98-395; DRT, Protein Sciences) at a final concentration of 20 nM. The final reaction volume in each well was 100 μL and the final compound concentration ranged from 10 μM-128 pM in 1% DMSO. The reaction mixture was allowed to incubate for 1-2 hours with gentle agitation at 25° C. To terminate the reaction, streptavidin-coated SPA beads (Amersham RPNQ0007; 50 μL of 0.5 mg beads dissolved in 165 mM EDTA) were then added to each well and incubation proceeded for an additional 15 minutes at 25° C. The plate was then centrifuged for ten minutes at 2000 rpm. Phosphorylation of the peptide substrate was measured using a Wallac 1450 Microbeta Plus Liquid Scintillation Counter. Using these procedures, all Examples demonstrated IC50s of less then 0.1 µM in both the Aurora 1 and Aurora 2 murine biochemical assays.

To determine the ability of compounds to inhibit Aurora Kinase 1 activity in cells, a capture ELISA measuring Aurora Kinase 1 autophosphorylation was developed in HT29 colon carcinoma cells (Yasui Y, et al 2004). Briefly, 15,000 cells/well were seeded in a 96-well collagen coated plates in RPMI+10% FBS and incubated at 37° C. in 5% $CO_2$ overnight. The following day, the cells were treated with 166 nM nacadazole compounds for 24 hours at 37° C. Synchronized cells were further treated with compounds for 2 hours. Compound dilutions were prepared from 0.1 mM DMSO stocks such that 1.1 µL of each dilution was added to obtain a final concentration ranging from 10 µM to 13 nM in one-third log steps. Following compound treatment, plates were centrifuged at 1000 rpm for 2 minutes and washed twice with 100 µL of cold sterile TBS. Cells were then lysed (100 µL of 150 mM NaCl, 20 mM Tris, pH 7.5, 1 mM EDTA, 1 mM EGTA, 1% Triton-x-100 plus protease and phosphatase inhibitors) by shaking at 4° C. for 1 hour. Cell lysates were transferred to plates pre-coated with anti-phospho mAur1 (Rockland, 600-401-677) and blocked with 5% blocker A in TBS from Meso Scale Discovery. After incubating for 1 hour at RT, plates were washed with 300 µL of TBST for a total of three times. The supernatant was removed and replaced with 50 µL of diluted primary antibody (anti-Aurora Kinase 1, Pharmingen, 611083) at 1:1000 in 2% blocker A in TBS and incubated at room temperature for 1 hour. The antibody buffer was removed from each well and washed three times with 300 µL of cold TBS-T (50 µM Tris pH 8.0, 138 mM NaCl, 2.7 mM KCL, 0.05% Tween 20). The wash buffer was replaced with 50 µL of secondary antibody (Sulfa TAG anti-mouse, Meso Scale Discovery) at 1:1000 in 2% blocker A and incubated at room temperature for 1 hour. For the final readout with the Sector 6000, 150 µL of reading buffer T was added and the plates were read immediately. Using this procedure, compounds all Examples demonstrate an IC50 less then 0.1 µM.

A. Operative Examples Relating to Pharmaceutical Compositions

The compounds according to the invention can be converted into pharmaceutical preparations as follows:

Tablet:

Composition:

100 mg of the compound of Example 1, 50 mg of lactose (monohydrate), 50 mg of maize starch (native), 10 mg of polyvinylpyrrolidone (PVP 25) (from BASF, Ludwigshafen, Germany) and 2 mg of magnesium stearate.

Tablet weight 212 mg, diameter 8 mm, curvature radius 12 mm.

Preparation:

The mixture of active component, lactose and starch is granulated with a 5% solution (m/m) of the PVP in water. After drying, the granules are mixed with magnesium stearate for 5 min. This mixture is molded using a customary tablet press (tablet format, see above). The molding force applied is typically 15 kN.

Suspension for Oral Administration:

Composition:

1000 mg of the compound of Example 1, 1000 mg of ethanol (96%), 400 mg of Rhodigel (xanthan gum from FMC, Pennsylvania, USA) and 99 g of water.

A single dose of 100 mg of the compound according to the invention is provided by 10 ml of oral suspension.

Preparation:

The Rhodigel is suspended in ethanol and the active component is added to the suspension. The water is added with stirring. Stirring is continued for about 6 h until the swelling of the Rhodigel is complete.

What is claimed is:

1. A compound having the formula (I):

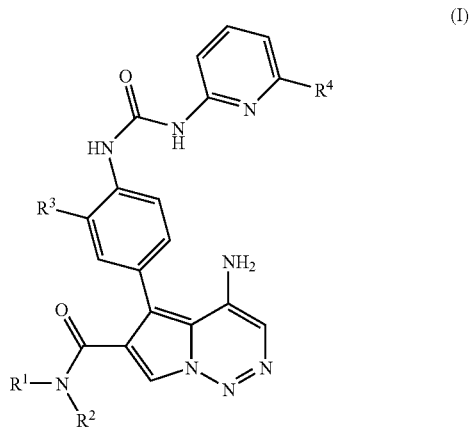

or a physiologically acceptable salt or stereoisomer thereof, wherein:

$R^1$ is -($C_1$-$C_4$)alkyl, -($C_1$-$C_4$)alkyl-$CF_3$, -($C_3$-$C_6$)cycloalkyl, or -($C_2$-$C_4$)alkyl-$NR^5R^6$;

$R^2$ is hydrogen or -($C_1$-$C_4$)alkyl;

$R^3$ is halogen;

$R^4$ is methyl or ethyl; and $R^5$ and $R^6$, may be the same or different, and are independently hydrogen, methyl, ethyl, or $R^5$ and $R^6$ may be taken together with the nitrogen to which they are bound to form a pyrrolidine ring.

2. The compound of claim 1, wherein $R^1$ is methyl, ethyl, n-propyl, sec-butyl, iso-butyl, tert-butyl, cyclopropyl, 2,2,2-trifluoroethyl, or 2-(dimethylamino)-ethyl.

3. The compound of claim 1, wherein $R^2$ is hydrogen.

4. The compound of claim 1, wherein $R^3$ is fluorine or chlorine.

5. The compound of claim 1, wherein $R^3$ is fluorine or chlorine and $R^4$ is methyl or ethyl.

6. The compound of claim 1, which is a salt of formula (I).

7. The compound of claim 6, wherein the salt is an acetate, an adipate, an alginate, an ascorbate, an aspartate, a benzoate, a benzenesulfonate, a bis(benzenesulfonate), a bisulfate, a butyrate, a bis(maleate), a fumarate, a hemi-fumarate, a citrate, a camphorate, a camphorsulfonate, a cinnamate, a cyclopentanepropionate, a digluconate, a dodecylsulfate, a ethanesulfonate, a fumarate, a glucoheptanoate, a glycerophosphate, a hemisulfate, a heptanoate, a hexanoate, a hydrochloride, a hydrobromide, a hydroiodide, a 2-hydroxyethanesulfonate, an itaconate, a lactate, a maleate, a mandelate, a methanesulfonate, a 2-naphthalenesulfonate, a nicotinate, a nitrate, an oxalate, a pamoate, a pectinate, a persulfate, a 3-phenylpropionate, a picrate, a pivalate, a propionate, a succinate, a sulfonate, a bis(methanesulfonate), a tartrate, a thiocyanate, a tosylate, or an undecanoate salt.

8. The compound of claim 7, wherein the salt is a bis (methanesulfonate), a hydrochloride, a bis(maleate), a hemifumarate, a hydrobromide, an oxalate, or a bis(benzenesulfonate) salt.

9. A compound having the IUPAC name:
4-amino-5-(3-fluoro-4-{[(6-methylpyridin-2-yl)carbamoyl]amino}phenyl)-N-methylpyrrolo[2,1-f][1,2,4]triazine-6-carboxamide;
4-amino-N-ethyl-5-(3-fluoro-4-{[(6-methylpyridin-2-yl)carbamoyl]amino}phenyl)pyrrolo[2,1-f][1,2,4]triazine-6-carboxamide;
4-amino-5-(3-fluoro-4-{[(6-methylpyridin-2-yl)carbamoyl]amino}phenyl)-N-propylpyrrolo[2,1-f][1,2,4]triazine-6-carboxamide;
4-amino-5-(3-fluoro-4-{[(6-methylpyridin-2-yl)carbamoyl]amino}phenyl)-N-(2,2,2-trifluoroethyl)pyrrolo[2,1-f][1,2,4]triazine-6-carboxamide;
4-amino-5-(3-fluoro-4-{[(6-methylpyridin-2-yl)carbamoyl]amino}phenyl)-N-isobutylpyrrolo[2,1-f][1,2,4]triazine-6-carboxamide;
4-amino-N-cyclopropyl-5-(3-fluoro-4-{[(6-methylpyridin-2-yl)carbamoyl]amino}phenyl)pyrrolo[2,1-f][1,2,4]triazine-6-carboxamide;
4-amino-N-ethyl-5-(3-fluoro-4-{[(6-methylpyridin-2-yl)carbamoyl]amino}phenyl)-N-methylpyrrolo[2,1-f][1,2,4]triazine-6-carboxamide;
4-amino-N-[2-(dimethylamino)ethyl]-5-(3-fluoro-4-{[(6-methylpyridin-2-yl)carbamoyl]amino}phenyl)pyrrolo[2,1-f][1,2,4]triazine-6-carboxamide;
4-amino-N-tert-butyl-5-(3-fluoro-4-{[(6-methylpyridin-2-yl)carbamoyl]amino}phenyl)pyrrolo[2,1-f][1,2,4]triazine-6-carboxamide;
4-amino-N-tert-butyl-5-(4-{[(6-ethylpyridin-2-yl)carbamoyl]amino}-3-fluorophenyl)pyrrolo[2,1-f][1,2,4]triazine-6-carboxamide;
4-amino-5-(4-{[(6-ethylpyridin-2-yl)carbamoyl]amino}-3-fluorophenyl)-N-(2,2,2-trifluoroethyl)pyrrolo[2,1-f][1,2,4]triazine-6-carboxamide;
4-amino-5-(3-chloro-4-{[(6-methylpyridin-2-yl)carbamoyl]amino}phenyl)-N-ethylpyrrolo[2,1-f][1,2,4]triazine-6-carboxamide;
4-amino-5-(3-chloro-4-{[(6-methylpyridin-2-yl)carbamoyl]amino}phenyl)-N-propylpyrrolo[2,1-f][1,2,4]triazine-6-carboxamide;
4-amino-5-(3-chloro-4-{[(6-methylpyridin-2-yl)carbamoyl]amino}phenyl)-N-cyclopropylpyrrolo[cyclopropylpyrrolo[2,1-f][1,2,4]triazine-6-carboxamide;
4-amino-5-(3-chloro-4-{[(6-methylpyridin-2-yl)carbamoyl]amino}phenyl)-N-[2-(dimethylamino)ethyl]pyrrolo[2,1-f][1,2,4]triazine-6-carboxamide;
4-amino-5-(3-chloro-4-{[(6-methylpyridin-2-yl)carbamoyl]amino}phenyl)-N-(2,2,2-trifluoroethyl)pyrrolo[trifluoroethyl)pyrrolo[2,1-f][1,2,4]triazine-6-carboxamide;
4-amino-5-(3-chloro-4-{[(6-ethylpyridin-2-yl)carbamoyl]amino}phenyl)-N-(2,2,2-trifluoroethyl)pyrrolo[2,1-f][1,2,4]triazine-6-carboxamide;
or a physiologically acceptable salt or stereoisomer thereof.

10. A salt having the IUPAC name:
4-amino-5-(3-fluoro-4-{[(6-methylpyridin-2-yl)carbamoyl]amino}phenyl)-N-(2,2,2-trifluoroethyl)pyrrolo[2,1-f][1,2,4]triazine-6-carboxamide dimethanesulfonate;
4-amino-5-(3-fluoro-4-{[(6-methylpyridin-2-yl)carbamoyl]amino}phenyl)-N-(2,2,2-trifluoroethyl)pyrrolo[2,1-f][1,2,4]triazine-6-carboxamide hydrochloride;
4-amino-5-(3-fluoro-4-{[(6-methylpyridin-2-yl)carbamoyl]amino}phenyl)-N-(2,2,2-trifluoroethyl)pyrrolo[2,1-f][1,2,4]triazine-6-carboxamide di[(2Z)-but-2-enedioate];
4-amino-5-(3-fluoro-4-{[(6-methylpyridin-2-yl)carbamoyl]amino}phenyl)-N-(2,2,2-trifluoroethyl)pyrrolo[2,1-f][1,2,4]triazine-6-carboxamide (2E)-but-2-enedioate (2:1);
4-amino-5-(3-fluoro-4-{[(6-methylpyridin-2-yl)carbamoyl]amino}phenyl)-N-(2,2,2-trifluoroethyl)pyrrolo[2,1-f][1,2,4]triazine-6-carboxamide hydrobromide;
4-amino-5-(4-{[(6-methylpyridin-2-yl)carbamoyl]amino}phenyl)-N-(2,2,2-trifluoroethyl)pyrrolo[2,1-f][1,2,4]triazine-6-carboxamide oxalate; or 4-amino-5-(4-{[(6-methylpyridin-2-yl)carbamoyl]amino}phenyl)-N-(2,2,2-trifluoroethyl)pyrrolo[2,1-f][1,2,4]triazine-6-carboxamide bisbenzenesulfonate.

11. A pharmaceutical composition comprising a compound according to claim 1 or a physiologically acceptable salt or stereoisomer thereof and a pharmaceutically acceptable diluent or carrier.

12. The pharmaceutical composition of claim 11 wherein the compound is present in a therapeutically effective amount.

13. The pharmaceutical composition of claim 11 further comprising at least one further active compound.

14. A packaged pharmaceutical composition comprising a container, the pharmaceutical composition of claim 11 and instructions for using the pharmaceutical composition to treat cancer of the breast in a mammal.

15. A method of treating cancer of the breast in a mammal comprising administering to a mammal in need thereof, a therapeutically effective amount of one or more compounds of claim 1.

* * * * *